US012576140B2

(12) United States Patent
Dickey et al.

(10) Patent No.: US 12,576,140 B2
(45) Date of Patent: Mar. 17, 2026

(54) CYCLOPHILIN 40 FOR REDUCTION OF NEUROTOXIC FIBRILS AND TREATMENT OF NEURODEGENERATIVE DISEASES

(71) Applicants: University of South Florida, Tampa, FL (US); The United States Government as Represented by the Department of Veterans Affairs, Washington, DC (US); Adria Dickey, Lutz, FL (US)

(72) Inventors: Chad Dickey, Lutz, FL (US); Jeremy Dustin Baker, Tampa, FL (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIR, Washington, DC (US)

( * ) Notice: Subject to any disclaimer, the term of this patent is extended or adjusted under 35 U.S.C. 154(b) by 1064 days.

(21) Appl. No.: 17/389,169

(22) Filed: Jul. 29, 2021

(65) Prior Publication Data

US 2021/0361753 A1    Nov. 25, 2021

Related U.S. Application Data

(62) Division of application No. 16/095,270, filed as application No. PCT/US2017/030140 on Apr. 28, 2017, now abandoned.

(60) Provisional application No. 62/329,317, filed on Apr. 29, 2016.

(51) Int. Cl.

| | |
|---|---|
| A61K 38/52 | (2006.01) |
| A61K 31/198 | (2006.01) |
| A61K 31/27 | (2006.01) |
| A61K 31/445 | (2006.01) |
| A61K 31/55 | (2006.01) |
| A61K 31/713 | (2006.01) |
| A61K 45/06 | (2006.01) |
| A61P 25/28 | (2006.01) |

(52) U.S. Cl.
CPC ............ *A61K 38/52* (2013.01); *A61K 31/198* (2013.01); *A61K 31/27* (2013.01); *A61K 31/445* (2013.01); *A61K 31/55* (2013.01); *A61K 31/713* (2013.01); *A61K 45/06* (2013.01); *A61P 25/28* (2018.01); *C12Y 502/01008* (2013.01)

(58) Field of Classification Search
CPC .. A61K 38/52; A61P 25/28; C12Y 502/01008
See application file for complete search history.

(56) References Cited

U.S. PATENT DOCUMENTS

| | | | |
|---|---|---|---|
| 2005/0209173 A1 | 9/2005 | Graef et al. | |
| 2014/0342979 A1 | 11/2014 | Weeks et al. | |

FOREIGN PATENT DOCUMENTS

| | | |
|---|---|---|
| CN | 1340537 A | 3/2002 |
| DE | 10327937 | 1/2004 |
| EP | 1212078 | 6/2005 |
| WO | 2005109004 | 11/2005 |
| WO | 2009018179 | 2/2009 |

OTHER PUBLICATIONS

Effects of memantine on cognition in patients with moderate to severe Alzheimer's disease: post-hoc analyses of ADAS-cog and SIB total and single-item scores from six randomized, double-blind, placebo controlled studies. Patrizia Mecocci, Anna Bladström, Karina Stender (2009) Int J Geriatr Psychiatry (Year: 2009).*
Adeno-Associated Virus Vectors in Clinical Trials, Barrie J. Carter, Human Gene Therapy 16:541-550 (May 2005) (Year: 2005).*
"A human enzyme can reduce neurotic amyloids in mouse model of dementia," [online], retrieved Jun. 18, 2019 retrieved from the internet, URL: https://hscweb3.hsc.usf.edu/blog/2017/06/27/human-enzyme-can-reduce-neurotoxic-amylodis-mouse-model-dementia/, pp. 1-3.
Abedin, A. et al. "Destabilization of human IAPP amyloid fibrils by proline mutations outside of the putative amyloidogenic domain: is there a critical amyloidogenic domain in human IAPP?" Journal of Molecular Biology, 2006, pp. 274-281, vol. 355.
Abisambra, J. F. et al. "Phosphorylation dynamics regulate Hsp27-mediated rescue of neuronal plasticity deficits in tau transgenic mice" The Journal of Neuroscience: The Official Journal of the Society for Neuroscience, 2010, pp. 15374-15382, vol. 30, No. 46.
Baker, J. D. et al. "Human cyclophilin 40 unravels neurotoxic amylodis" PLoS Biol, 2017, pp. 1-22, e2001336, vol. 15, No. 6.
Blackburn, E. A. et al. "Cyclophilin40 isomerase activity is regulated by a temperature-dependent allosteric interaction with Hsp90" Biosci Rep., Oct. 2015: e00258, vol. 35, No. 5.
Blair, L. J. et al. "Accelerated neurodegeneration through chaperone-mediated oligomerization of tau" The Journal of Clinical Investigation, 2013, pp. 4158-4169, vol. 123, No. 10.
Blair, L. J. et al. "The emerging role of peptidyl-prolyl isomerase chaperones in tau oligomerization, amyloid processing and Alzheimer's disease" Journal of Neurochemistry, 2015, pp. 1-13, vol. 133, No. 1.
Braak, H. et al. "Neuropathological stageing of Alzheimer-related changes" Acta neuropathological, 1991, pp. 239-259, vol. 82.

(Continued)

*Primary Examiner* — Teresa E Knight
*Assistant Examiner* — Kodye Lee Abbott
(74) *Attorney, Agent, or Firm* — HUSCH BLACKWELL LLP

(57) ABSTRACT

The present invention concerns the use of peptidyl-prolyl isomerase cyclophilin 40 (CyP40) for reduction of neurotoxic fibrils and treatment and prevention of neurodegenerative diseases associated with amyloid fibril aggregation. Aspects of the invention include compositions, methods, dosage forms, and kits for treating or preventing a neurodegenerative disease or condition associated with amyloid fibril aggregation in a human or animal subject, and for disaggregating neurofibrillary aggregates in vitro or in vivo, using CyP40, or a biologically active fragment thereof.

13 Claims, 11 Drawing Sheets

Specification includes a Sequence Listing.

(56) References Cited

OTHER PUBLICATIONS

Bradford, A. et al. "Missed and Delayed Diagnosis of Dementia in Primary Care: Prevalence and Contribution Factors" Alzheimer Dis Assoc Disord., 2009, pp. 306-314, vol. 23, No. 4.

Brenda website: https://www.brenda-enzymes.org/search_result.php?quicksearch=1&noOfResults=10&a=9&W[2]=cyclophilin-40&T[2]=2&V[8]=1 downloaded Apr. 24, 2021 (Year: 2021).

Chiba, T. et al. "Amyloid fibril formation in the context of full-length protein: effects of proline mutations on the amyloid fibril formation of beta2-microglobulin" The Journal of Biological Chemistry, 2003, pp. 47016-47024, vol. 278, No. 47.

Davis, T. L. et al. "Structural and biochemical characterization of the human cyclophilin family of peptidyl-prolyl isomerases" PLoS biology 8, 2010, e1000439 (1-16 pages), vol. 8, No. 7.

Dickey, C. et al. "Aging Analysis Reveals Slowed Tau Turnover and Enhanced Stress Responses in a Mouse Model of Tauopathy" The American Journal of Pathology, 2009, pp. 228-238, vol. 174, No. 1.

Eisenberg, D. et al. "The amyloid state of proteins in human disease" Cell, Mar. 16, 2012, pp. 1188-1203, vol. 148, No. 6.

English translation of DE10327937 (A1) published Jan. 9, 2004 downloaded from Espacenet on Feb. 1, 2021 (Year: 2004).

Gao, X. et al. "Human Hsp70 Disaggregase Reverses Parkinson's-Linked alpha-Synuclein Amyloid Fibrils" Molecular Cell, Sep. 3, 2015, pp. 781-793, vol. 59, No. 5.

Giustiniani, J. et al. "Immunophilin FKBP52 induces Tau-P301L filamentous assembly in vitro and modulates its activity in a model of tauopathy" Proceedings of the National Academy of Sciences of the United States of America, 2014, pp. 4584-4589, vol. 111, No. 12.

Goldschmidt, L. et al. "Identifying the amylome, proteins capable of forming amyloid-like fibrils" Proceedings of the National Academy of Sciences of the United States of America, Feb. 23, 2010, pp. 3487-3492, vol. 107, No. 8.

Gomex-Rio, M. et al. "Diagnosis of Neurodegenerative diseases: The clinical approach" Curr Alzheimer Res., 2016, 99. 469-474, vol. 13, No. 5.

Gordon, M. N. et al. "Exaggerated astrocyte reactivity after nigrostriatal deafferentation in the aged rat" The Journal of comparative neurology, 1997, pp. 106-119, vol. 388.

Hodak, H. et al. "The peptidyl-prolyl isomerase and chaperone Par27 of Bordetella pertussis as the prototype for a new group of parvulins" Journal of Molecular Biology, 2008, pp. 414-426, vol. 376.

Jackrel, M. E. et al. "Potentiated Hsp104 variants antagonize diverse proteotoxic misfolding events" Cell, 2014, pp. 170-182, vol. 156.

Jackrel, M. E. et al. "Potentiated Hsp104 variants suppress toxicity of diverse neurodegenerative disease-linked proteins" Disease Models & Mechanisms, 2014, pp. 1175-1184, vol. 7.

Jaru-Ampornpan, P. et al. "Mechanism of an ATP-independent protein disaggregase: II. distinct molecular interactions drive multiple steps during aggregate disassembly" The Journal of Biological Chemistry, 2013, pp. 13431.13445, vol. 288, No. 19.

Jinwal, U. K. et al. "The Hsp90 cochaperone, FKBP51, increases Tau stability and polymerizes microtubules" The Journal of Neuroscience: The Official Journal of the Society of Neuroscience, 2010, pp. 591-599, vol. 30, No. 2.

Koikkalainen, J. et al. "Differential diagnosis of neurodegenerative diseases using structural MRI data" Neuroimage Clin., 2016, pp. 435-439, vol. 11.

Machine Translation of CN-1340537-A (publication date Mar. 20, 2021) downloaded from Espacenetpatent search on Apr. 23, 2021 (Year: 2002).

Morimoto, A. et al. "Aggregation and neurotoxicity of mutant amyloid beta (A beta) peptides with proline replacement: importance of turn formation at positions 22 and 23" Biochemical and Biophysical Research Communications, 2002, pp. 306-311, vol. 295.

Morimoto, A. et al. "Analysis of the secondary structure of beta-amyloid (Abeta42) fibrils by systematic proline replacement" The Journal of Biological Chemistry, 2004, pp. 52781-52788, vol. 279, No. 50.

Murray, A. N. et al. "Surface absorption considerations when working with amyloid fibrils in multiwell plates and Eppendorf tubes" Protein Science: A Publication of the Protein Society, 2013, pp. 1531-1541, vol. 22.

Nillegoda, N. B. et al. "Crucial HSP70 co-chaperone complex unlocks metazoan protein disaggregation" Nature, 2015, pp. 247-251, vol. 524, No. 7564.

O'Leary, J. C. et al. "Phenothiazine-mediated rescue of cognition in tau transgenic mice requires neuroprotection and reduced soluble tau burden" Molecular Neurodegeneration, 2010, pp. 1-11, vol. 5, No. 45.

Ramsden, M. et al. "Age-dependent neurofibrillary tangle formation, neuron loss, and memory impairment in a mouse model of human tauopathy (P301L)" The Journal of Neuroscience: The Official Journal of the Society of Neuroscience, 2005, pp. 10637-10647, vol. 25, No. 46.

Santacruz, K. et al. "Tau suppression in a neurodegenerative mouse model improves memory function" Science, 2005, pp. 476-481, vol. 309, No. 5733.

Spires, T.L. et al. "Region-specific dissociation of neuronal loss and neurofibrillary pathology in a mouse model of auopathy" The American Journal of Pathology, 2006, pp. 1598-1607, vol. 168, No. 5.

Stoessi, A. J. "Neuroimaging in the early diagnosis of neurodegenerative disease" Translational Neurodegeneration, 2012, pp. 1-5.

The Cambridge Dictionary Website: https://dictionary.cambridge.org/us/dictionary/english/kit downloaded Apr. 24, 2021 (Year: 2021).

Torbeev, V. Y. et al. "Both the cis-trans equilibrium and isomerization dynamics of a single proline amide modulate β2-microglobulin amyloid assembly" Proceedings of the National Academy of Sciences of the United States of America, Dec. 10, 2013, pp. 20051-20056, vol. 110, No. 50.

Usenovic, M. et al. "Internalized Tau Oligomers Cause Neurodegeneration by Inducing Accumulation of Pathogenic Tau in Human Neurons Derived from Induced Pluripotent Stem Cells" The Journal of Neuroscience: The Official Journal of the Society for Neuroscience, Oct. 21, 2015, pp. 14234-14250, vol. 35, No. 42.

Ward, B. K. et al. "A Structure-based Mutational Analysis of Cyclophilin 40 Identifies Key Residues in the Core Tetratricopeptide Repeat Domain That Mediate Binding to Hsp90" The Journal of Biological Chemistry, 2002, pp. 40799-40809, vol. 277, No. 43.

Ward, S. M. et al. "Tau oligomers and tau toxicity in neurodegenerative disease" Biochemical Society Transactions, 2012, pp. 667-671, vol. 40, No. 4.

* cited by examiner

CYCLOPHILIN 40 FOR REDUCTION OF NEUROTOXIC FIBRILS AND TREATMENT OF NEURODEGENERATIVE DISEASES

CROSS-REFERENCE TO RELATED APPLICATIONS

The present application is a divisional of U.S. application Ser. No. 16/095,270, filed Oct. 19, 2018, which is the National Stage of International Application No. PCT/US2017/030140, filed Apr. 28, 2017, which claims the benefit of U.S. Provisional Application Ser. No. 62/329,317, filed Apr. 29, 2016, each of which is hereby incorporated by reference herein in its entirety, including any figures, tables, nucleic acid sequences, amino acid sequences, or drawings.

GOVERNMENT SUPPORT

This invention was made with government support NS073899 awarded by National Institutes of Health. The government has certain rights in the invention.

REFERENCE TO A SEQUENCE LISTING SUBMITTED VIA EFS-WEB

This application includes an electronically submitted Sequence Listing in .txt format. The txt file contains a sequence listing entitled "2N32536-SeqList-as filed. TXT" and was created on Jul. 29, 2021 and is 3,715 bytes in size. The Sequence Listing contained in this .txt file is part of the specification and is hereby incorporated herein in its entirety.

BACKGROUND OF THE INVENTION

Protein complexes with disaggregase activity have recently been discovered in eukaryotic organisms. Disaggregation is important because many diseases result from aberrant protein aggregation, particularly in the brain. Hsp104 and cpSRP43 possess disaggregation activity, but there are no known mammalian orthologues [1]. More recently, it was shown that the chaperone Hsp70 works in a multi-protein complex with ATP to promote disaggregation of various amyloidogenic substrates.

Many mammalian proteins have intrinsic sequences that promote amyloid fibril formation. This is believed to be a natural process to allow proteins to autonomously prevent the formation of more toxic amorphous intermediate structures (2,3). However, in some cases such as neurodegenerative disease, amyloid formation is an aberrant process that can promote proteotoxicity (4). Recent evidence suggests endogenous protein complexes have the ability to dissolve these potentially toxic amyloidogenic structures (5). This work has not only shed light on novel endogenous pathways of disaggregation, but also suggests that these proteins could be exploited to mitigate disease pathogenesis. For example, the yeast disaggregase Hsp104 utilized ATP hydrolysis to disaggregate a variety of human proteins in a yeast model (6,7). More recently, the metazoan Hsp70/DnaJ/Hsp110 complex was found to work with ATP to disaggregate amyloid substrates in vitro (8). However, the dynamic and ubiquitous nature of aggregation and disaggregation in cells suggests that a more energy-efficient process might exist, one that does not require ATP.

BRIEF SUMMARY OF THE INVENTION

The peptidyl-prolyl isomerase cyclophilin 40 (CyP40), encoded by the PPID gene, has been identified to be an ATP-independent human disaggregase. CyP40, independent of any co-factors, dissolved fibrillized aggregates of two disease-relevant amyloids: the microtubule associated protein tau and α-synuclein. Overexpression of CyP40 in the rTg4510 tau transgenic mouse brain was neuroprotective and decreased fibrillar and oligomeric tau species. The disaggregating activity of CyP40 appeared selective for those proteins possessing proline residues, and was dependent on the prolyl isomerase activity of the enzyme. This work shows that a low energy human disaggregase can independently and selectively protect neurons from proteotoxicity in the mammalian brain.

The present invention concerns compositions and methods for treating or preventing a neurodegenerative disease or condition associated with amyloid fibril aggregation, and for disaggregating neurofibrillary aggregates in vitro or in vivo, using peptidyl-prolyl isomerase cyclophilin 40 (CyP40), or a biologically-active fragment thereof.

Thus, one aspect of the invention concerns a method for treating or preventing a neurodegenerative disease or condition associated with amyloid fibril aggregation, the method comprising administering an effective amount of CyP40, or a biologically-active fragment thereof, to a subject in need thereof.

Another aspect of the invention concerns a method for disaggregating neurofibrillary aggregates, comprising contacting the aggregates with an effective amount of CyP40, or a biologically-active fragment thereof, in vitro or in vivo.

Another aspect of the invention concerns a composition comprising CyP40, or a biologically-active fragment thereof; and an agent effective for treating or preventing a neurodegenerative disease or condition associated with amyloid fibril aggregation

BRIEF DESCRIPTION OF THE DRAWINGS

FIG. 1A shows a schematic representation of the hypothesized mechanism showing amyloid-forming protein monomer aggregating into an ordered mature amyloid fibril. Upon the addition of peptidyl-prolyl isomerases (PPIases), key proline residues at structurally important locations may be isomerized leading to destabilization of secondary structure and subsequent disaggregation. FIG. 1B depicts Thioflavin T fluorescence measured 3 hours after CyP40 addition, revealed a significant decrease in fluorescence (p=0.0020), while the addition of CyPA, FKBP51, or FKBP52 did not produce significant differences. FIG. 1C shows a bar graph representation of the time point 3 hours post addition of PPIase. FIG. 1D shows 60.000× transmission electron microscopy of fibrils (left) showed linear and curved fibrils while CyP40 treated fibrils (right) were amorphous and lack linear structure (scale bar 400 nm and 600 nm for inset).

FIG. 2A shows a schematic depicting the timeline of rTg4510 pathology and experimental design. FIG. 2B shows results of a Western blot comparing the insoluble (Ins) and soluble (Sol) fractions from hippocampi of AAV9-GFP (n=8) and AAV9-CyP40 (n=8) injected mice. FIG. 2C shows quantification of the relative insoluble tau levels from FIG. 2B indicated a significant decrease in CyP40 treated mice (p=0.0016, scale bar 2000 μm and 500 μm for inset). FIGS. 2D and 2E show levels of total tau were significantly reduced in CyP40 treated mice (p=0.0011, scale bar 2000 μm and 500 μm for

Figure 2A:
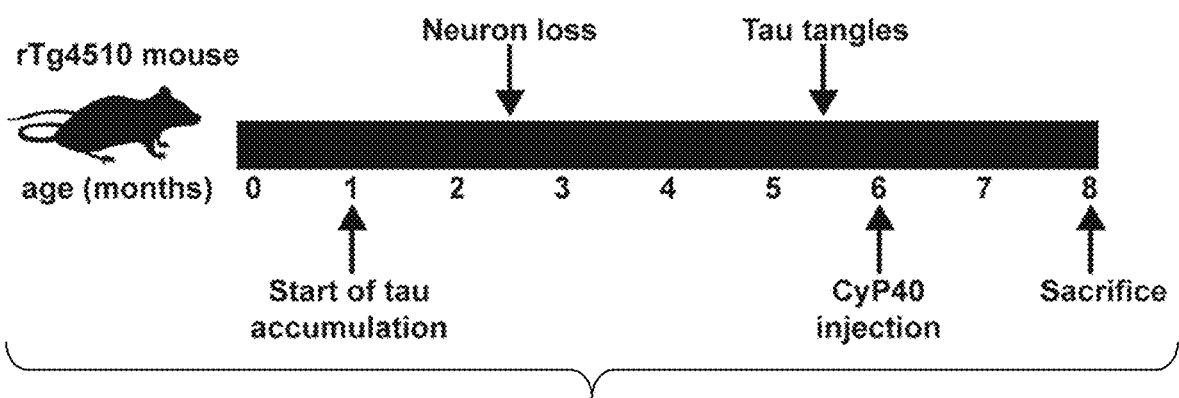
FIGS. 2A-2K. CyP40 lowered insoluble tau and oligomeric tau levels and promoted neuronal health in a mouse model overexpressing P301L tau.
Figure 2B:
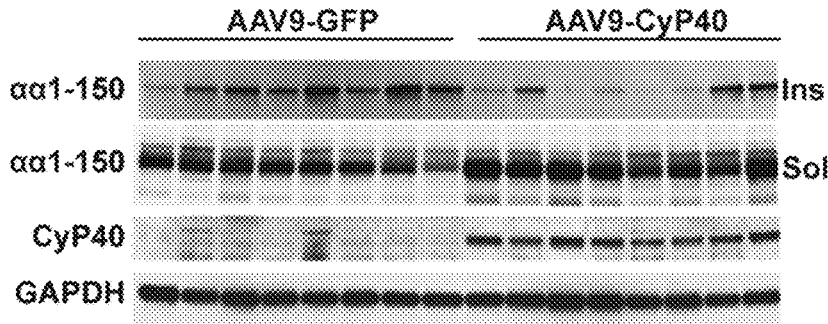
Figure 2C:
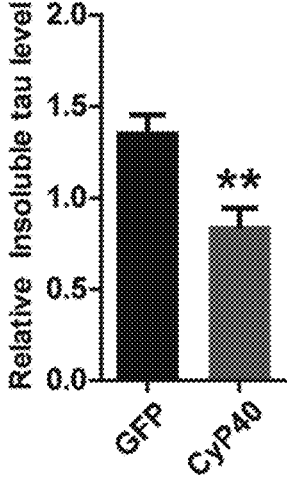
Figures 2D, 2E, 2F, 2G:
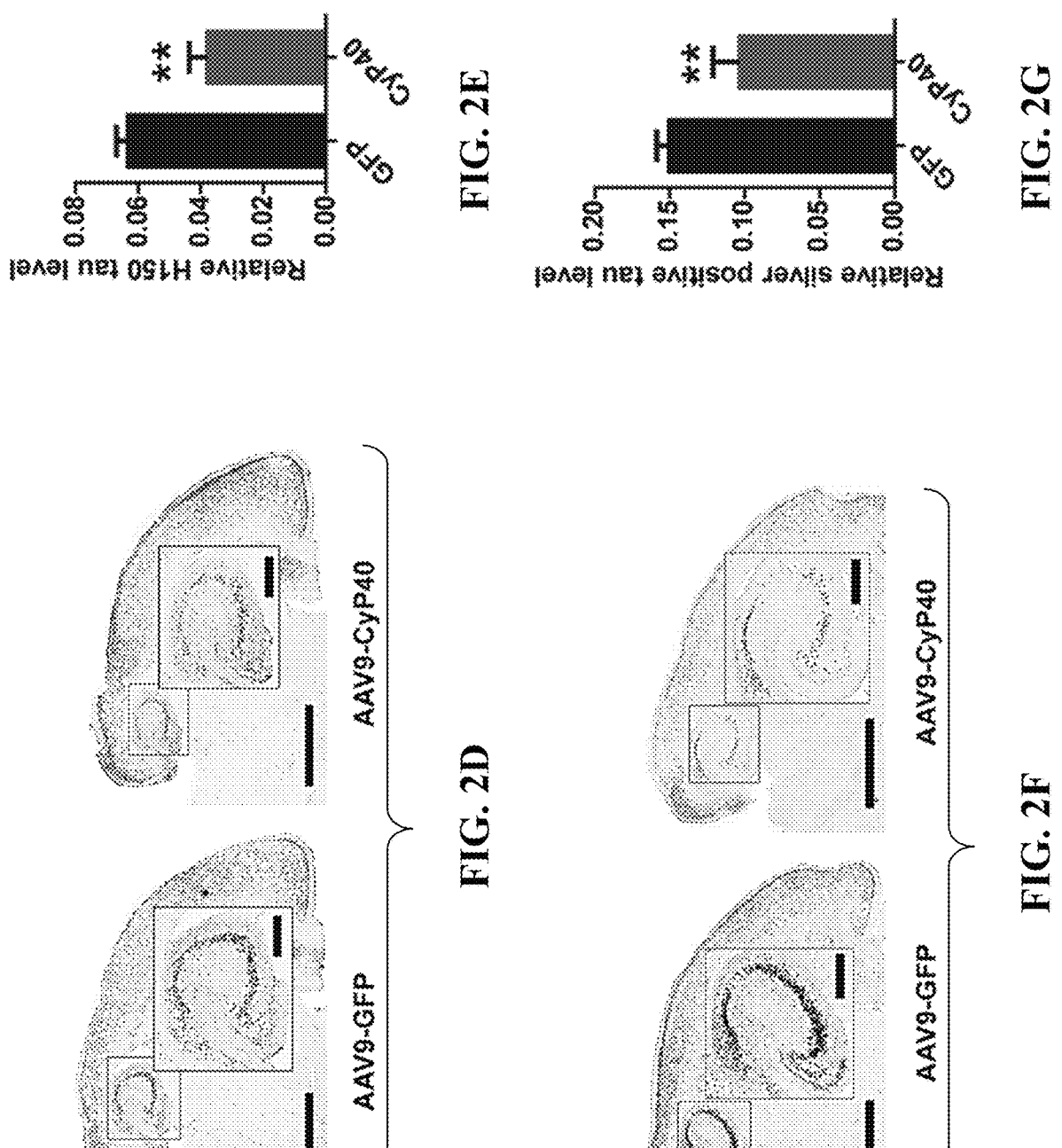
Figures 2H, 2I, 2J, 2K:
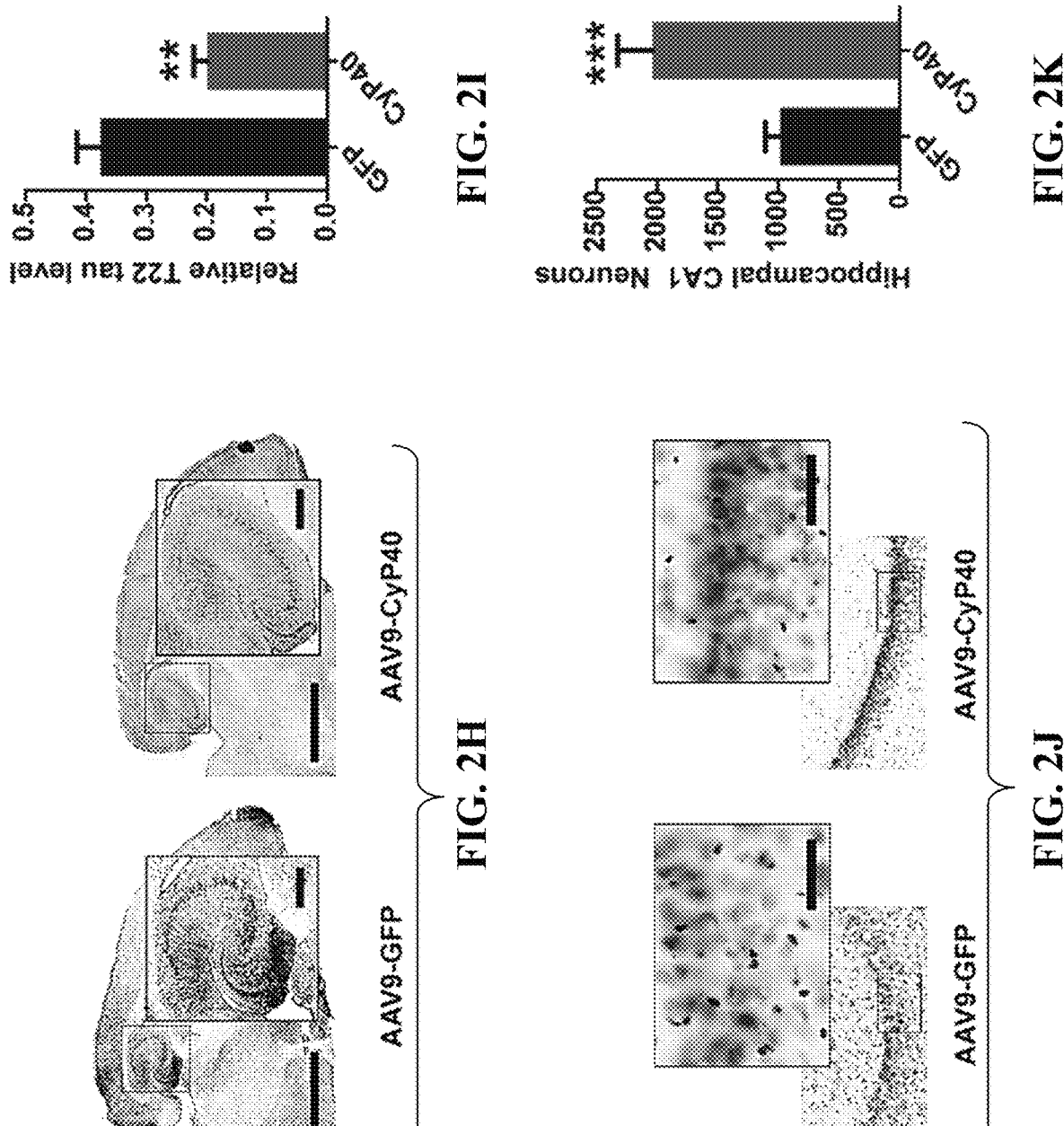

3 inset). FIGS. 2F and 2G show results of Gallyas silver staining of hippocampal sections from GFP and CyP40 injected mice revealed a significant decrease in silver-positive tau (p=0.0228, scale bar 2000 μm and 500 μm for inset). FIGS. 2H and 2I show levels of oligomeric tau, as measured by the T22 antibody, were significantly decreased (p=0.0011) following CyP40 treatment (scale bar 2000 μm and 500 μm for inset). FIGS. 2J and 2K show results of unbiased stereology, indicating a significant increase in the number of CA1 neurons in CyP40 treated hippocampi (p=0.0001, scale bar 125 μm).

Figures 3A, 3B:
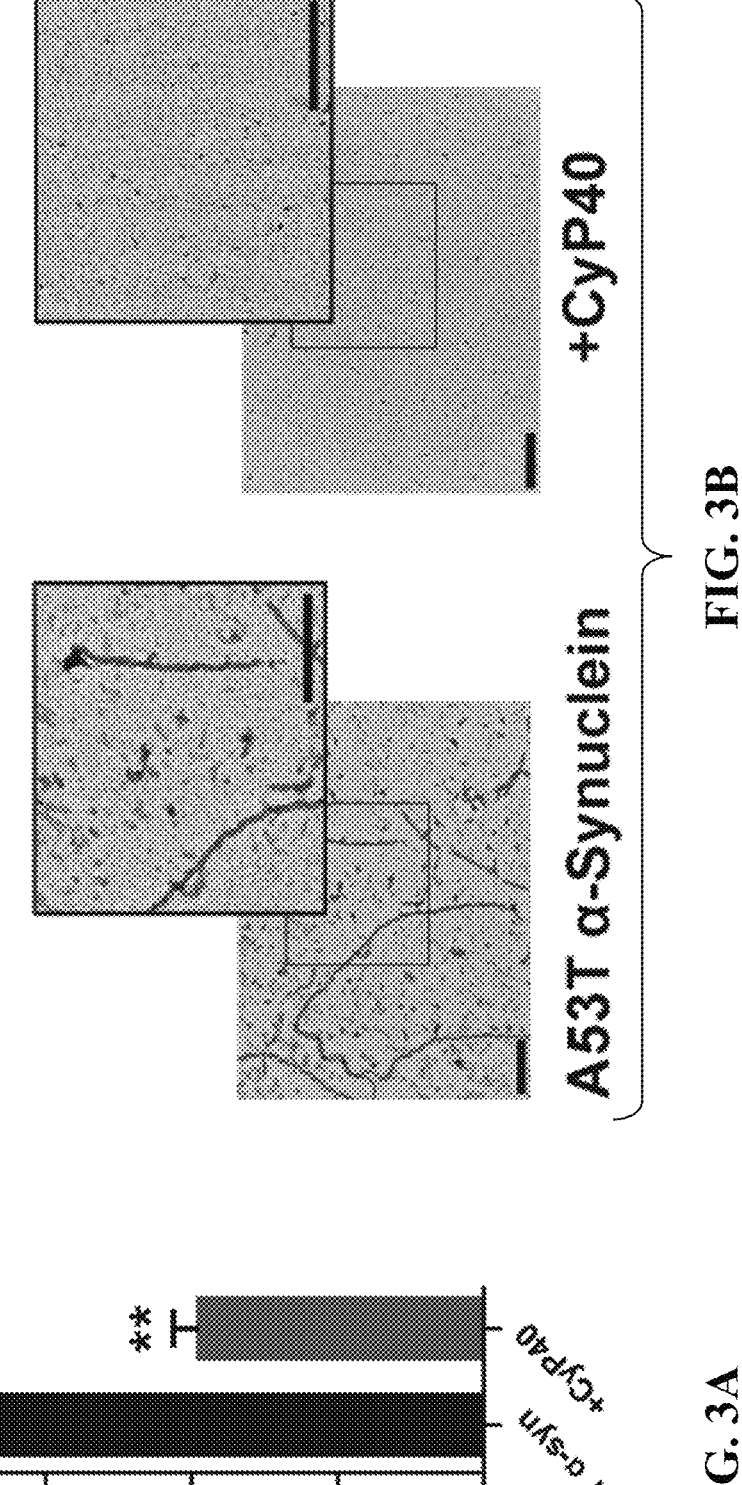
Figures 3C, 3D:
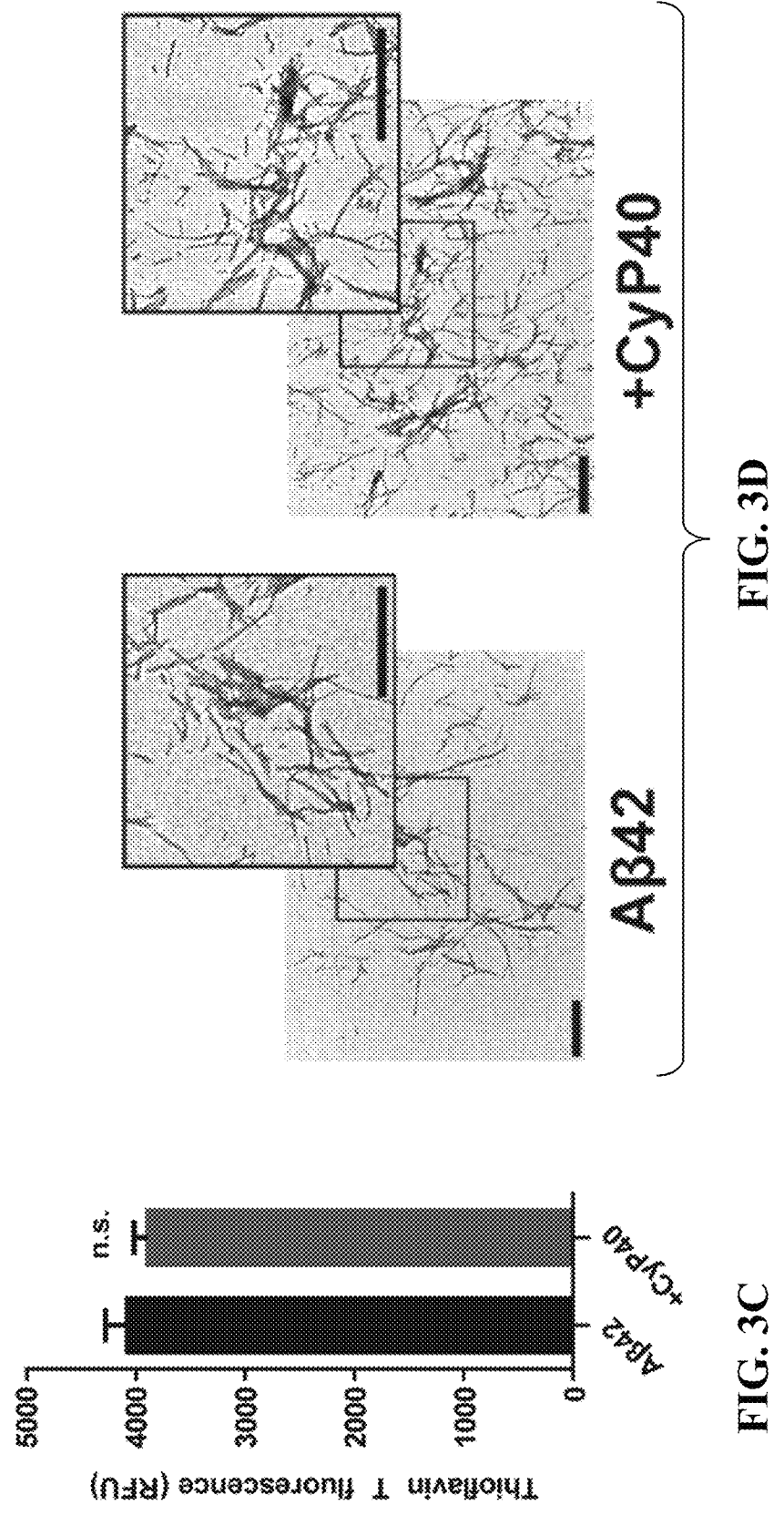
Figures 1, 2, 3E, 3F, 3G:
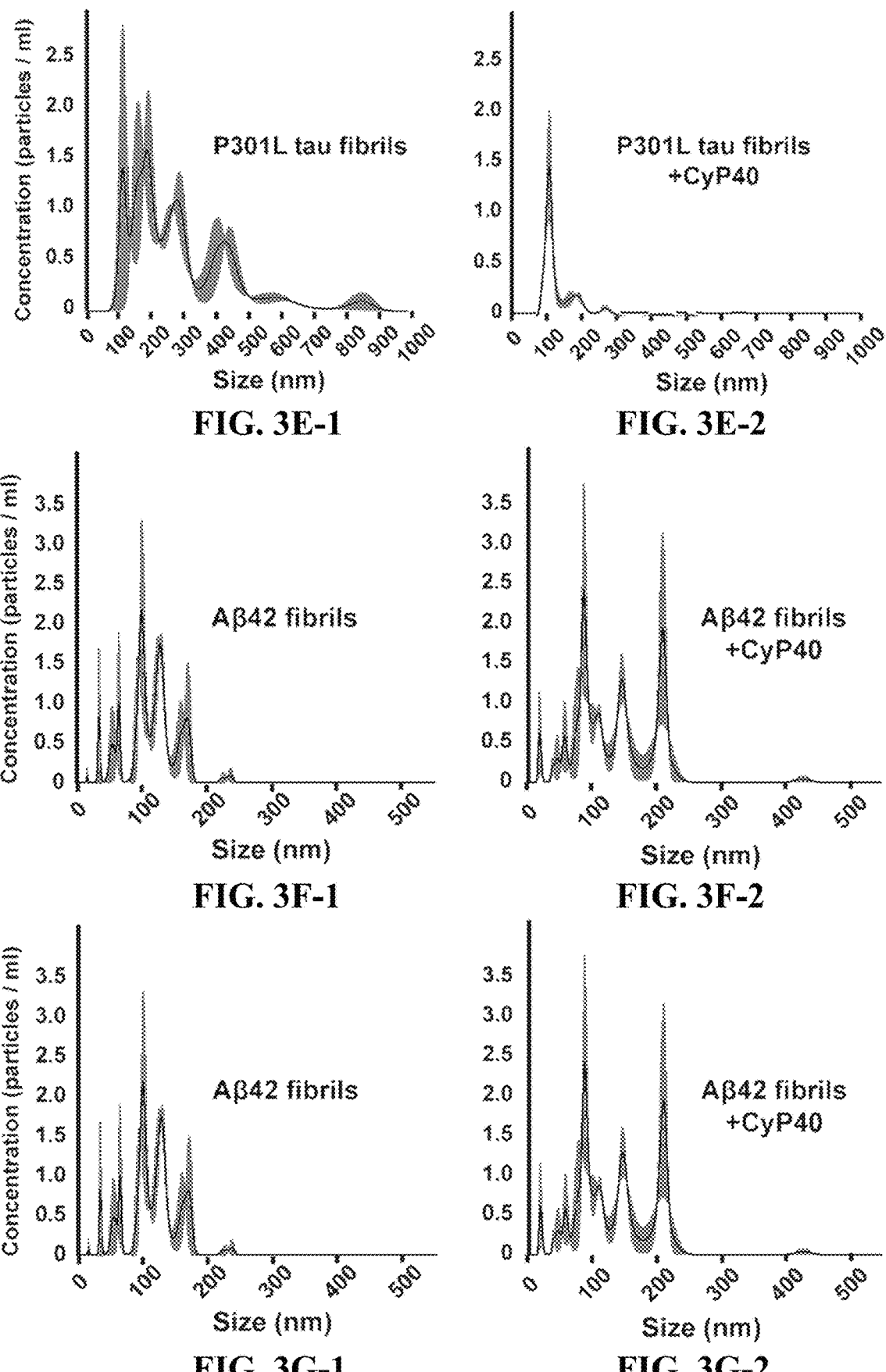

FIGS. 3A, 3B, 3C, 3D, 3E-1, 3E-2, 3F-1, 3F-2, 3G-1, 3G-2. CyP40 disaggregates A53T α-synuclein, but not Aβ42 mature fibrils. FIG. 3A shows results of incubation of mature A53T α-synuclein fibrils with CyP40 significantly decreased Thioflavin T Fluorescence (p=0.0008). FIG. 3B shows transmission electron microscopy (TEM) images of A53T α-synuclein fibrils with or without addition of CyP40 (60,000× magnification, scale bar 400 nm) (FIG. 3C) ThT fluorescence of Aβ42 fibrils was not significantly affected by CyP40 treatment. FIG. 3D shows TEM of mature Aβ42 fibrils showed no apparent change in morphology following CyP40 co-incubation (60,000× magnification, scale bar 400 nm). FIGS. 3E-1 and 3E-2 show NTA of tau fibrils incubated with CyP40 shows less aggregate populations in the 300-850 nm range. FIGS. 3F-1 and 3F-2 show NTA of A53T α-synuclein fibrils incubated with CyP40 shows a lack of aggregate populations in the 200-450 nm range. FIGS. 3G-I and 3G-2 show NTA did not reveal an apparent change in size distribution of fibrils between Aβ42 control and CyP40-treated samples.

Figure 4A:
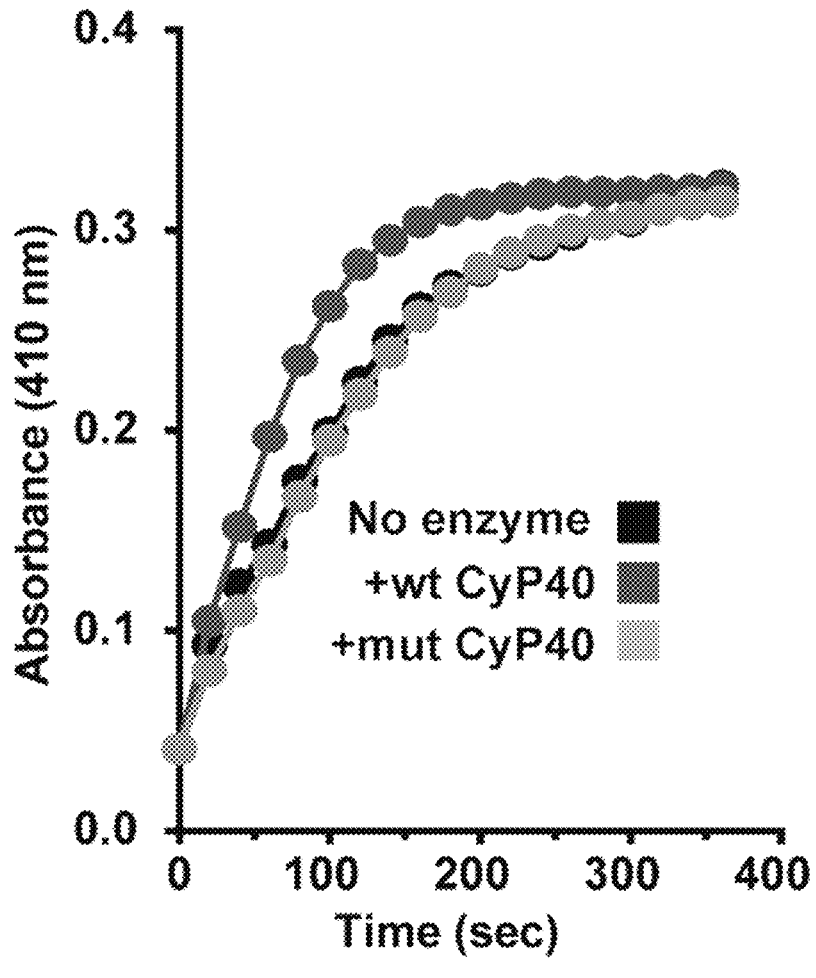
Figure 4B:
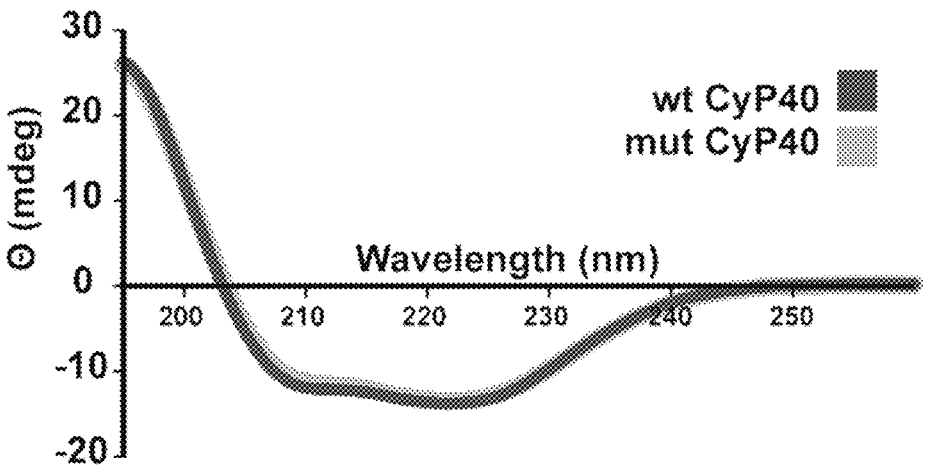
Figures 4C, 4D:
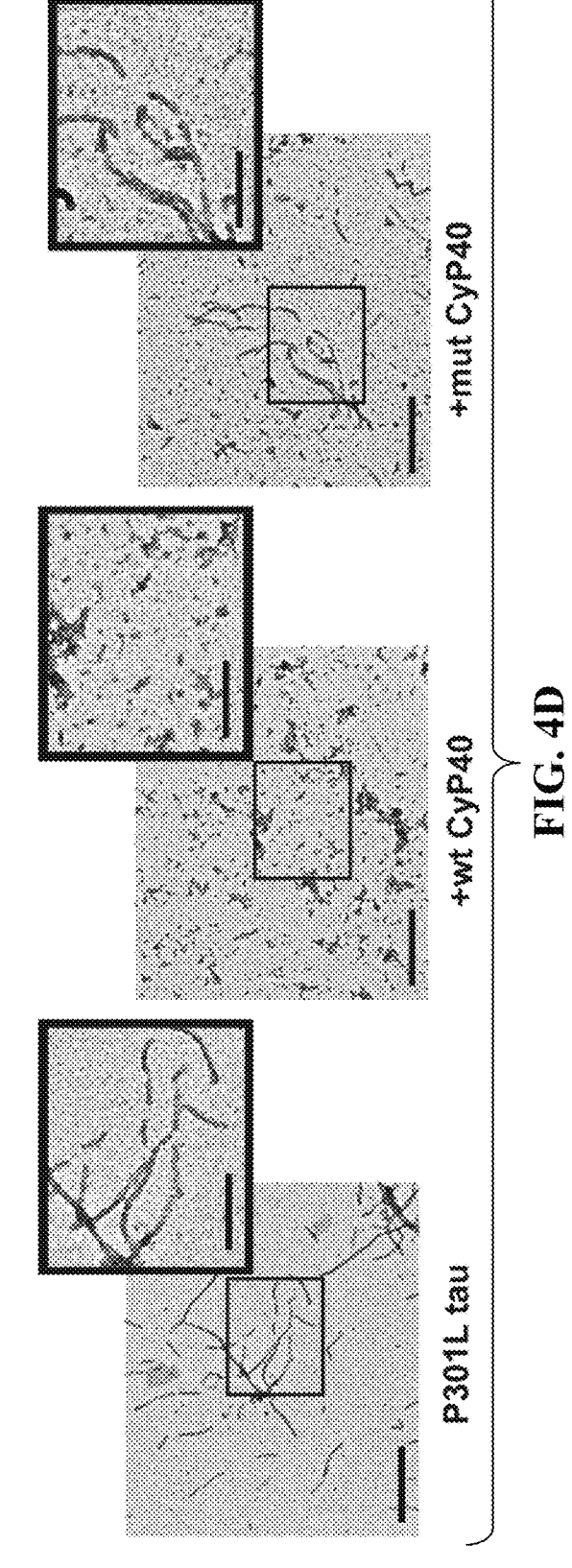
Figure 4E:
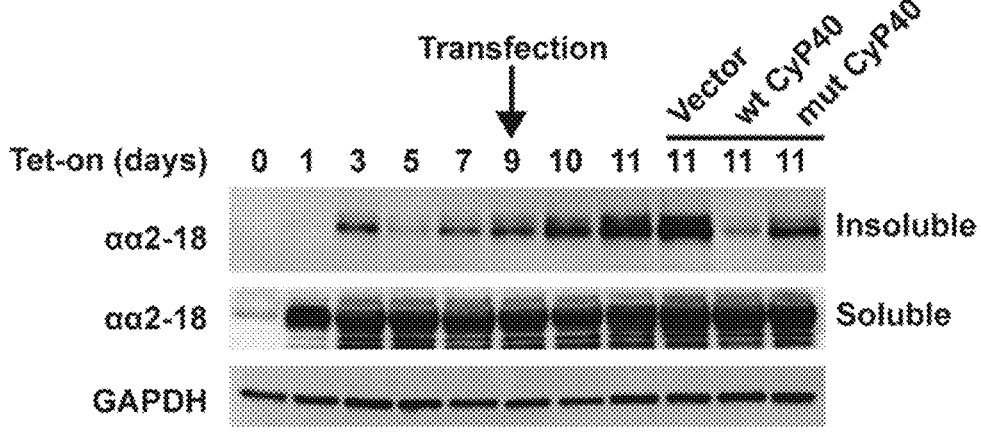
Figure 4F:
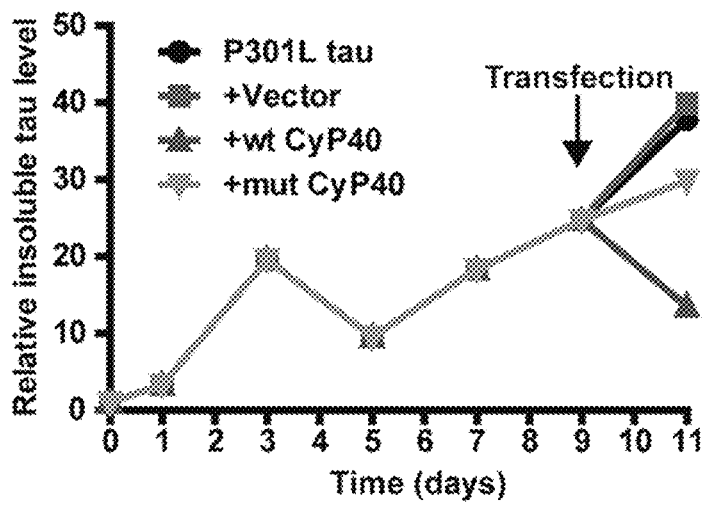

FIGS. 4A-4F. CyP40-mediated disaggregation depends on prolyl-isomerase activity of the enzyme as shown in vitro and in an inducible cell model overexpressing P301L tau. FIG. 4A shows results of a coupled chymotrypsin assay, revealing isomerase activity in wild-type (wt) CyP40, but not mutant (mut) CyP40 as compared to the no enzyme control. FIG. 4B shows that circular dichroism did not show differences between wt CyP40 and mut CyP40 secondary structures. FIG. 4C shows ThT fluorescence significantly decreased by wt CyP40 treatment of tau fibrils (p=0.0265), but not by mut CyP40 treatment (FIG. 4D) Transmission electron microscopy showed straight and curved mature tau fibers 300-600 nm in length that were disintegrated by co-incubation with wt CyP40, but not mut CyP40 treatment (scale bar 400 nm, 200 nm inset). FIG. 4E shows inducible HEK cells overexpressing tau P301L (iHEK-P301L) that were induced on day 1 show increasing insoluble tau levels after 11 days of overexpression. Vector-transfected and mut CyP40-transfected cells did not affect insoluble tau levels, while wt CyP40-transfected cells showed a decrease in insoluble tau levels as depicted in line graph (FIG. 4F).

BRIEF DESCRIPTION OF THE SEQUENCES

SEQ ID NO:1 is an amino acid sequence of a human CyP40 polypeptide; mshpspqakp snpsnprvffdvdiggervg riv-ielfadi vpktaenfra lctgekgigh ttgkplhfkg cpfhriikkf miqggdfsnq ngtggesiyg ekfedenfhy khdregllsm anagrmtngs qffittvptp hldgkhvvfg qvikgigvar ilenvevkge kpaklcviae cgelkegddg gifpkdgsgd shpdfpedad idlkdvdkil litedlknig ntfflksqnwe maikkyaevl ryvdsskavi etadraklqp ialscvlnig acklkmsnwq gaidscleal eldpsntkal yrraggwqgl keydgaladl kkaqgiaped kaiqaellkv kqkikaqkdk ekavyakmfa

4

(NCBI Accession Number Q08752, version Q08752.3 GI:729274)

DETAILED DESCRIPTION OF THE INVENTION

The present invention concerns materials and methods for treating or preventing a neurodegenerative disease or condition associated with amyloid fibril aggregation, and for disaggregating neurofibrillary aggregates in vitro or in vivo, using peptidyl-prolyl isomerase cyclophilin 40 (CyP40), or a biologically-active fragment thereof.

Thus, one aspect of the invention concerns a method for treating or preventing a neurodegenerative disease or condition associated with amyloid fibril aggregation, the method comprising administering an effective amount of CyP40, or a biologically-active fragment thereof, to a subject in need thereof. In some embodiments, prior to said administering, the method further comprises identifying the subject as having a neurodegenerative disease or condition associated amyloid fibril aggregation. Methods for diagnosing neurodegenerative diseases or conditions are known in the art can be utilized, such as imaging and other tests (30-32).

Another aspect of the invention concerns a method for disaggregating neurofibrillary aggregates, comprising contacting the aggregates with an effective amount of CyP40, or a biologically-active fragment thereof, in vitro or in vivo.

Another aspect of the invention concerns a composition comprising CyP40, or a biologically-active fragment thereof; and an agent effective for treating or preventing a neurodegenerative disease or condition associated with amyloid fibril aggregation.

In some embodiments of the methods, compositions, dosage forms, and kits of the invention, the CyP40 polypeptide is human CyP40 (SEQ ID NO: 1), or a biologically active fragment or variant thereof.

In one embodiment, a method of the invention for treating or preventing a neurodegenerative disease or a condition associated with aggregation of amyloid fibrils, comprises administering an effective amount of CyP40, or a biologically-active fragment or variant thereof, or a polynucleotide encoding the same, to a human or animal subject in need thereof. In some embodiments of the method for treating or preventing a neurodegenerative disease or condition, the disease or condition is characterized the presence of neurofibrillary aggregates of proline-containing fibrils. In one embodiment of the method for treating or preventing a neurodegenerative disease or condition, the disease or condition is characterized by the presence of neurofibrillary aggregates of protein tau and/or α-synuclein in a cell, such as a neuronal or glial cell. Diseases and conditions contemplated within the scope of the invention include, but are not limited to, Alzheimer's disease, gangliogliomas and gangliocytomas, argyrophilic grain dementia, corticobasal degeneration, dementia pugilistica, frontotemporal dementia with parkinsonism linked to chromosome17, Pick's disease, Hallervorden-Spatz disease, myotonic dystrophy, Niemann-Pick disease (type C), Parkinsonism-dementia complex of Guam, postencephalitic parkinsonism, prion diseases (some), progressive subcortical gliosis, and progressive supranuclear palsy. The disease or condition may be early onset or late onset. For example, in the case of Alzheimer's disease, the disease may be early onset, late onset, or familial Alzheimer's disease.

In a specific embodiment of the method, CyP40 is administered to the human or non-human animal subject or is delivered to a target cell in the subject via a polynucleotide encoding a CyP40 polypeptide, or a biologically active fragment or variant thereof. In one embodiment, the CyP40 polypeptide is a human CyP40 (GenBank Accession No. Q08752, version Q08752.3 GI:729274). In a specific embodiment, the human CyP40 polypeptide comprises the amino acid sequence of SEQ ID NO: 1, or a biologically active fragment or variant thereof. In one embodiment, a method of the invention comprises injecting (e.g., via stereotaxic injection) a polynucleotide expression construct of the invention comprising a polynucleotide encoding a CyP40 polypeptide directly into neural tissue and/or cells of a human or non-human animal subject. In a specific embodiment, the expression construct is an adeno-associated viral construct. Optionally, other biologically active agents such as drugs and therapeutics, useful in treating neurodegenerative diseases and conditions can also be administered to the human or animal. The other drugs and therapeutics can be administered to the human or animal prior to, at the same time (co-administered), or subsequent to administration of the CyP40 polypeptide or polynucleotide encoding the same. Examples of other drugs or therapeutics that can be administered include, but are not limited to, donepezil (Aricept), galantamine (Razadyne), rivastigmine (Exelon), memantine (Akatinol), and L-dopa.

In some embodiments, the other biologically active agent is another agent that is effective in treating or preventing a neurodegenerative disease, such as those associated with amyloid fibril aggregation. In some embodiments, the other biologically active agent is another agent having fibril disaggregation activity, such as chaperone Hsp70. In some embodiments, the other biologically active agent is a polypeptide having disaggregation activity, such as a chaperone Hsp70 polypeptide, and the other biologically active agent is coupled to a CyP40 polypeptide, or a biologically active fragment thereof, as a complex, and the polypeptide complex, or polynucleotide encoding the polypeptide complex, is administered to the subject or brought into contact with the amyloid fibrils in, vitro or in vivo.

The subject invention also concerns a method for disaggregating neurofibrillary aggregates, comprising contacting the aggregates with an effective amount of CyP40, or a biologically active fragment thereof, in vitro or in vivo. In some embodiments, the neurofibrillary aggregates comprise proline-containing fibrils. In some embodiments, the neurofibrillary aggregates comprise protein tau and/or α-synuclein.

In some embodiments, a CyP40 polypeptide, or a biologically active fragment or variant thereof, or a polynucleotide encoding the same, is contacted with or provided to a target cell. The target cell can be a neuron or a glial cell. In a specific embodiment, a CyP40 polypeptide is delivered to the target cell via a polynucleotide encoding a CyP40 polypeptide, or a biologically active fragment or variant thereof. In one embodiment, the CyP40 polypeptide is a human CyP40 polypeptide. In a specific embodiment, the human CyP40 polypeptide comprises the amino acid sequence of SEQ ID NO:1, or a biologically active fragment or variant thereof. In one embodiment, a method of the invention comprises injecting (e.g., via stereotaxic injection) a polynucleotide expression construct of the invention comprising a polynucleotide encoding a CyP40 polypeptide directly into neural tissue or cells of a human or non-human animal subject. In a specific embodiment, the expression construct is an adeno-associated viral construct. An expression construct of the invention can be designed to provide for constitutive expression of a CyP40 polypeptide in a target cell or tissue. Optionally, other biologically active agents such as drugs and therapeutics useful in methods for disaggregating neurofibrillary aggregates in a target cell can also be contacted or provided to a target cell. The other biologically active agents can be provided or contacted prior to, at the same time (co-administered), or subsequent to administration of the CyP40 polypeptide or polynucleotide encoding the same. Examples of other drugs or therapeutics that can be administered include, but are not limited to, paclitaxel, a statin, lithium, inhibitors of cyclin-dependent kinase 5, and methylthionine chloride.

The subject invention also concerns compositions comprising i) a CyP40 polypeptide, or a biologically active fragment or variant thereof, and/or ii) a polynucleotide encoding an a CyP40 polypeptide, or a biologically active fragment or variant thereof. The polynucleotide can be an expression construct that provides for expression of a CyP40 polypeptide in a target cell. In one embodiment, the CyP40 polypeptide is a human CyP40 polypeptide. In a specific embodiment, the human CyP40 polypeptide comprises the amino acid sequence of SEQ ID NO:1, or a biologically active fragment or variant thereof. Compositions of the invention can also comprise other biologically active agents such as drugs or therapeutics, examples of which include, but are not limited to, donepezil (Aricept), galantamine (Razadyne), rivastigmine (Exelon), memantine (Akatinol), paclitaxel (Taxol), a statin, lithium, inhibitors of cyclin-dependent kinase 5, methylthionine chloride, and L-dopa.

In some embodiments, the polypeptides and polynucleotides in the composition, and/or administered to the subject, are in isolated form.

The polypeptides of the present invention can be formulated into pharmaceutically-acceptable salt forms. Pharmaceutically acceptable salt forms include the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically acceptable base addition salts include sodium, potassium, calcium, ammonium, and magnesium salts. Pharmaceutically acceptable salts of the polypeptides of the invention can be prepared using conventional techniques.

The subject invention also concerns polynucleotide expression constructs that comprise a polynucleotide of the present invention comprising a nucleotide sequence encoding a CyP40 polypeptide of the present invention. In one embodiment, the CyP40 polypeptide is a human CyP40 polypeptide. In one embodiment, the polynucleotide encodes a polypeptide comprising the amino acid sequence shown in SEQ ID NO:1, or a fragment or variant thereof that exhibits CyP40's disaggregation activity.

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMPS promoter, TRP-1 promoter, murine mammary tumor virus long terminal repeat promoter, STAT promoter, or an immunoglobulin promoter can be used in the expression construct. In one embodiment, the expression construct comprises a promoter that can drive expression of a polynucleotide of the invention in neuronal or glial cells. Promoters effective in neurons that can be used in the present invention include gamma-aminobutyric acid type A receptor $\beta_1$ subunit promoter (U.S. Pat. No. 6,066, 726), zebrafish HuC promoter (U.S. Published Application No. 20040093630), and cellular adhesion molecule ICAM-4 promoter (U.S. Pat. No. 5,753,502) (see also U.S. Pat. No. 6,040,172).

Expression constructs of the invention may optionally contain a transcription termination sequence, a translation termination sequence, signal polypeptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal polypeptides are a group of short amino terminal sequences that encode information responsible for the relocation of an operably linked polypeptide to a wide range of post-translational cellular destinations, ranging from a specific organelle compartment to sites of protein action and the extracellular environment. Targeting a polypeptide to an intended cellular and/or extracellular destination through the use of operably linked signal polypeptide sequence is contemplated for use with the polypeptides of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, CA). A specific vector contemplated by the present invention is an adeno-associated virus.

Polynucleotides, vectors, and expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Feigner et al., 1987). Synthetic cationic lipids (LIPOFECTIN, Invitrogen Corp., La Jolla, CA) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

The present invention includes biologically active fragments and variants of CYP40 polypeptides and encoding polynucleotides. Thus, polynucleotides and polypeptides of the subject invention can also be defined in terms of more particular identity and/or similarity ranges with those sequences exemplified herein, such as SEQ ID NO: 1. The sequence identity with sequences exemplified herein, such as SEQ ID NO: 1, will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 05, 96, 97, 98, or 990% as compared to a sequence exemplified herein, such as SEQ ID NO:1. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules (encoding polypeptides of the invention) having sequences which are sufficiently homologous with the polynucleotide sequences encoding a polypeptide of the invention so as to permit hybridization with that sequence under standard stringent conditions and standard methods (Maniatis, T. et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A. et al., 1983):

$$Tm=81.5\ C+16.6\ Log\ [Na+]+0.41(\%\ G+C)-0.61(\%\ formamide)-600/length\ of\ duplex\ in\ base\ pairs.$$

Washes are typically carried out as follows:
(1) Twice at room temperature for 15 minutes in 1×SSPE, 0.1% SDS (low stringency wash).
(2) Once at Tm-20 C for 15 minutes in 0.2×SSPE, 0.1% SDS (moderate stringency wash).

In some embodiments, the biologically active variant has one or both of the following characteristics: retains prolyl isomerase activity, and retains the isomerase domain. In some embodiments, the biologically active variant is a biologically active variant of human CyP40 (SEQ ID NO:1) that has one or more of the following characteristics: retains prolyl isomerase activity; retains the isomerase domain; and greater than 60%, greater than 75%, greater than 80%, greater than 0%, greater than 95% sequence identity, or greater than 98% sequence identity to SEQ ID NO:1. The structure of human CyP40 protein has been described and is incorporated herein by reference in its entirety (27, 33-34).

The subject invention also contemplates biologically active fragments of full-length CyP40 polypeptides and polynucleotides that encode such fragments. In some embodiments, the biologically active fragment has one or both of the following characteristics: retains prolyl isomerase activity, and retains the isomerase domain. In some embodiments, the biologically active fragment is a biologically active fragment of full length human CyP40 (SEQ ID NO:1) that has one or both of the following characteristics: retains prolyl isomerase activity, and retains the isomerase domain (27, 33-34).

As used herein, in the context of fragments and variants of CyP40, the term "biologically active" refers to CYP40's amyloid fibril disaggregation activity. Methods for determining the capacity for disaggregation activity, which may be used for assessing variant and fragment sequences, are described herein.

As used herein, the term "biologically active agent" refers to agents such as drugs and biologics that are non-inert and have some effect on the body.

As used herein, the terms "nucleic acid", "polynucleotide", and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences (e.g., biologically active fragments). It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the sequences coding for a polypeptide of the invention. The polynucleotide includes both the sense and antisense strands as either individual strands or in the duplex.

In one embodiment, an effective amount of a polypeptide, polynucleotide, and/or composition of the present invention is administered to a subject having a neurodegenerative disorder or condition associated with amyloid fibril aggregation and who is in need of treatment thereof. The subject can be a human or other mammal, such as a dog, cat, or horse, or other animals having the disorder. Means for administering and formulating polypeptides and polynucleotides for administration to a patient are known in the art, examples of which are described herein. Polypeptides, polynucleotides, and/or compositions of the invention can be delivered to a cell either through direct contact of polypeptide or polynucleotide with the cell or via a carrier means. In one embodiment, a polypeptide or polynucleotide of the invention comprises an attached group that enhances cellular uptake of the polypeptide. In one embodiment, the polypeptide or polynucleotide is attached to an antibody that binds to a targeted cell. In another embodiment, the polypeptide or polynucleotide is encapsulated in a liposome. Polypeptides can also be delivered using a polynucleotide that encodes a subject polypeptide. Any polynucleotide having a nucleotide sequence that encodes a polypeptide of the invention is contemplated within the scope of the invention. In one embodiment, the polynucleotide is delivered to the cell where it is taken up and the polynucleotide is transcribed into RNA and the RNA is translated into the encoded polypeptide.

Therapeutic application of the subject polypeptides and polynucleotides, and compositions containing them, can be accomplished by any suitable therapeutic method and technique presently or prospectively known to those skilled in the art. The polypeptides and polynucleotides can be administered by any suitable route known in the art including, for example, oral, intramuscular, intraspinal, intracranial, nasal, rectal, parenteral, subcutaneous, or intravenous routes of administration. Administration of the polypeptides and polynucleotides of the invention can be continuous or at distinct intervals as can be readily determined by a person skilled in the art.

Compounds and compositions useful in the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive polypeptide or polynucleotide is combined with a suitable carrier in order to facilitate effective administration of the composition. The compositions used in the present methods can also be in a variety of forms. These include, for example, solid, semisolid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject polypeptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the polypeptide or polynucleotide of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the polypeptide or polynucleotide based on the weight of the total composition including carrier or diluent.

The compounds and molecules of the subject invention can also be administered utilizing liposome technology, slow release capsules, implantable pumps, and biodegradable containers. These delivery methods can, advantageously, provide a uniform dosage over an extended period of time.

The subject polypeptides and polynucleotides of the invention can also be modified by the addition of chemical groups, such as PEG (polyethylene glycol). PEGylated polypeptides typically generate less of an immunogenic response and exhibit extended half-lives in vivo in comparison to polypeptides that are not PEGylated when administered in vivo. Methods for PEGylating proteins and polypeptides known in the art (see, for example, U.S. Pat. No. 4,179,337). The subject polypeptides and polynucleotides can also be modified to improve cell membrane permeability. In one embodiment, cell membrane permeability can be improved by attaching a lipophilic moiety, such as a steroid, to the polypeptide or polynucleotide. Other groups known in the art can be linked to polypeptides or polynucleotides of the present invention.

The subject invention also concerns a packaged dosage formulation comprising in one or more packages, packets, or containers at least one polypeptide or polynucleotide and/or composition of the subject invention formulated in a pharmaceutically acceptable dosage. The package can contain discrete quantities of the dosage formulation, such as tablet, capsules, lozenge, and powders. The quantity of polypeptide or polynucleotide in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg.

The subject invention also concerns kits comprising in one or more containers a composition, compound, or molecule of the present invention. In one embodiment, a kit contains a polypeptide or polynucleotide of the present invention. In a specific embodiment, a kit comprises a polypeptide comprising the amino acid sequence shown in SEQ ID NO:1, or a fragment or variant of the polypeptide that exhibits CyP40 disaggregation activity. A kit of the invention can also comprise one or more compounds, biological molecules, or drugs. In one embodiment, a kit of the invention can comprise a polypeptide or polynucleotide of the invention, and optionally comprises one or more of a drug or composition used in treating a neurodegenerative disease or condition. Examples of other drugs or therapeutics include, but are not limited to, donepezil (Aricept), galantamine (Razadyne), rivastigmine (Exelon), memantine (Akatinol), paclitaxel (Taxol), a statin, lithium, inhibitors of cyclin-dependent kinase 5, methylthionine chloride, and L-dopa.

Polypeptides having one or more substitutions of amino acids other than those specifically exemplified in the subject polypeptides are also contemplated within the scope of the present invention. For example, one or more non-natural amino acids can be substituted for the amino acids of a polypeptide of the invention, so long as the polypeptide having substituted amino acids retains substantially the same activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid. γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Nonnatural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a polypeptide having an amino acid of one class is replaced with another amino acid of the same class fall within the scope of the subject invention so long as the polypeptide having the substitution still retains substantially the same biological activity as a polypeptide that does not have the substitution. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Single letter amino acid abbreviations are defined in Table 2

TABLE 2

| Letter Symbol | Amino Acid |
| --- | --- |
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

The methods and compositions of the present invention can be used in the treatment of humans and non-human animals. The animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

As used herein, "treat" is intended to mean administer an agent to a subject, such as a human or non-human mammal (for example, a non-human animal model), in order to prevent or delay a worsening of the effects of a condition, or to partially or fully reverse the effects of the condition, such as neurodegenerative disease or a condition associated with amyloid fibril aggregation. In some embodiments, the condition is characterized by the presence of neurofibrillary aggregates of the microtubule associated protein tau and/or alpha-synuclein.

As used herein, "prevent" is intended to mean prophylaxis, or to reduce or minimize the chance that a subject who has an increased susceptibility for developing a condition will develop the condition, or to delay the onset of the condition, such as neurodegenerative disease or a condition associated with amyloid fibril aggregation. In some embodiments, the condition is characterized by the presence of neurofibrillary aggregates of the microtubule associated protein tau and/or alpha-synuclein.

As used herein, "effective amount" of an agent, such as a polypeptide or a polynucleotide encoding the polypeptide, is intended to mean a sufficient amount of the agent to provide the desired effect. The exact amount required will vary, depending on the subject, species, age, and general condition of the subject, the severity of disease (or underlying genetic defect) that is being treated, the particular agent used, its mode of administration, and the like. An appropriate "effective amount" may be determined by one of ordinary skill in the art using routine experimentation.

As used herein, "isolated polypeptide" or "purified polypeptide" is intended to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full-length proteins and/or polypeptides.

As used herein, the terms "peptide", "polypeptide", and "protein" are used interchangeably and intended to mean both short peptides of from 2 to 10 amino acid residues, oligopeptides of from 11 to 370 amino acid residues, polypeptides of more than 370 amino acid residues, and full-length proteins. The peptides may occur naturally or be synthetically constructed.

As used herein, "isolated nucleic acid molecule", "purified nucleic acid molecule", or "isolated polynucleotide" or "purified polynucleotide" is intended to mean DNA that is free of the genes that, in the naturally-occurring genome of the organism from which the DNA of the invention is derived, flank the gene. The term therefore includes, for example, a recombinant DNA which is incorporated into or otherwise associated with a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid molecule" or "isolated polynucleotide" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

EXEMPLIFIED EMBODIMENTS

Embodiment 1. A method for treating or preventing a neurodegenerative disease or condition associated with amyloid fibril aggregation, said method comprising administering an effective amount of peptidyl-prolyl isomerase cyclophilin 40 (CyP40), or a biologically-active fragment thereof, to a human or animal subject in need thereof.

Embodiment 2. The method according to embodiment I, wherein said method further comprises identifying a subject as one in need of treatment.

Embodiment 3. The method according to embodiment I or 2, wherein the disease or condition is characterized by the presence of neurofibrillary aggregates of the microtubule associated protein tau and/or α-synuclein.

Embodiment 4. The method according to any one of embodiments 1 to 3, wherein the disease or condition is Alzheimer's disease, gangliogliomas, gangliocytomas, argyrophilic grain dementia, corticobasal degeneration, dementia pugilistica, frontotemporal dementia with parkinsonism linked to chromosome17, Pick's disease, Hallervorden-Spatz disease, myotonic dystrophy, Niemann-Pick disease (type C), Parkinsonism-dementia complex of Guam, post-encephalitic parkinsonism, prion diseases, progressive subcortical gliosis, or progressive supranuclear palsy.

Embodiment 5. The method according to any one of embodiments 1 to 4, wherein the CyP40, or a biologically active fragment thereof, is administered to the subject orally, nasally, rectally, parenterally, subcutaneously, intramuscularly, intraspinal, intracranially, or intravenously.

Embodiment 6. The method according to any one of embodiments 1 to 5, wherein the CyP40, or a biologically fragment thereof, is administered to the subject as a polynucleotide encoding the CyP40, or the biologically active fragment thereof.

Embodiment 7. The method according to any one of embodiments 1 to 6, wherein the polynucleotide is provided in an expression construct.

Embodiment 8. The method according to any one of embodiments 1 to 7, wherein the CyP40 is a human CyP40.

Embodiment 9. The method according to embodiment 6, wherein the polynucleotide is injected directly into neural tissue and/or cells of the subject.

Embodiment 10. The method according to embodiment 7, wherein the expression construct comprises a promoter that provides for expression of the polynucleotide in neurons or glial cells.

Embodiment 11. The method according to embodiment 7, wherein the expression construct is an adeno-associated viral construct.

Embodiment 12. The method according to any one of embodiments 1 to 11, wherein said method further comprises administering a biologically active agent used in treating neurodegenerative diseases and/or conditions to the subject.

Embodiment 13. The method according to embodiment 12, wherein the biologically active agent is administered prior to, or at the same time as, or subsequent to, administration of the CyP40, or the biologically active fragment thereof.

Embodiment 14. The method according to embodiment 12 or 13, wherein the biologically active agent is one or more of donepezil, galantamine, rivastigmine, memantine, or L-dopa.

Embodiment 15. The method according to any preceding embodiment, wherein the subject has the neurodegenerative disease or condition at the time of said administering, and the CyP40, or a biologically-active fragment thereof, is administered as therapy.

Embodiment 16. The method according to any one of embodiments 1 to 14, wherein the subject does not have the neurodegenerative disease or condition at the time of said administering, and the CyP40, or a biologically-active fragment thereof, is administered as prophylaxis.

Embodiment 17. A method for disaggregating neurofibrillary aggregates, comprising contacting the aggregates with an effective amount of peptidyl-prolyl isomerase cyclophilin 40 (CyP40), or a biologically-active fragment thereof, in vitro or in vivo.

Embodiment 18. The method of embodiment 17, wherein the neurofibrillary aggregates comprise microtubule associated protein tau and/or et-synuclein.

Embodiment 19. The method according to embodiment 17 or 18, wherein said contacting is in vivo and comprises administering the CyP40, or a biologically active fragment thereof, to a human or animal subject, and wherein the CyP40, or a biologically active fragment thereof, is administered to the subject orally, nasally, rectally, parenterally, subcutaneously, intramuscularly, intraspinal, intracranially, or intravascularly (e.g., intravenously).

Embodiment 20. The method according to any one of embodiments 17 to 19, wherein said contacting is in vivo and comprises administering the CyP40, or a biologically active fragment thereof, to a human or animal subject, and wherein the CyP40, or a biologically fragment thereof, is administered as a polynucleotide encoding the CyP40, or the biologically active fragment thereof.

Embodiment 21. The method according to embodiment 20, wherein the polynucleotide is provided in an expression construct.

Embodiment 22. The method according to any one of 17 to 21, wherein the CyP40 is a human CyP40 Embodiment 23. The method according to embodiment 20 or 21, wherein the polynucleotide is injected directly into neural tissue and/or cells of the subject.

Embodiment 24. The method according to embodiment 23, wherein the expression construct comprises a promoter that provides for expression of the polynucleotide in neurons or glial cells.

Embodiment 25. The method according to embodiment 21, wherein the expression construct is an adeno-associated viral construct.

Embodiment 26. The method according to any one of embodiments 17 to 25, wherein said method further comprises administering a biologically active agent used in treating neurodegenerative diseases and/or conditions to the subject.

Embodiment 27. The method according to embodiment 26, wherein the biologically active agent is administered prior to, or at the same time as, or subsequent to, administration of the CyP40, or the biologically active fragment thereof.

Embodiment 28. The method according to embodiment 26, wherein the biologically active agent is one or more of donepezil, galantamine, rivastigmine, memantine, or L-dopa.

Embodiment 29. A composition comprising a peptidyl-prolyl isomerase cyclophilin 40 (CyP40) polypeptide, or a biologically active fragment thereof; or a polynucleotide encoding a CyP40 polypeptide, or a biologically active fragment thereof.

Embodiment 30. The composition of embodiment 29, wherein said composition comprises a physiologically acceptable buffer, carrier, and/or diluent.

Embodiment 31. The composition of embodiment 29 or 30, further comprising an agent effective for treating or preventing a neurodegenerative disease or condition associated with amyloid fibril aggregation.

Embodiment 32. The composition of any one of embodiment 29 to 31, further comprising an agent having amyloid fibril disaggregation activity in vitro or in vivo.

Embodiment 33. A packaged dosage formulation comprising at least one of i) a CyP40 polypeptide, or a biologically active fragment thereof; and/or ii) a polynucleotide encoding a CyP40 polypeptide, or a biologically active fragment thereof; in a pharmaceutically acceptable dosage in one or more packages, packets, or containers.

Embodiment 34. The packaged dosage formulation according to embodiment 33, wherein said CyP40 polypeptide or said polynucleotide is provided as a tablet, capsule, lozenge, or powder.

Embodiment 35. The packaged dosage formulation according to embodiment 33, wherein said polynucleotide is provided in an expression construct.

Embodiment 36. The packaged dosage formulation according to embodiment 35, wherein said expression construct comprises a promoter that provides for expression of said polynucleotide in neurons or glial cells.

Embodiment 37. The packaged dosage formulation according to any one of embodiments 33 to 36, wherein said one or more packages, packets, or containers further comprise a biologically active agent useful in treating neurodegenerative disease or condition.

Embodiment 38. The packaged dosage formulation according to any one of embodiments 33 to 37, wherein said one or more packages, packets, or contains further comprise a biologically active agent useful for disaggregating neurofibrillary aggregates.

Embodiment 39. A kit comprising in one or more containers a CyP40 polypeptide, or a biologically active fragment thereof, and/or a polynucleotide encoding said CyP40 polypeptide, or said biologically active fragment thereof.

Embodiment 40. The kit according to embodiment 39, wherein said polynucleotide is provided in an expression construct.

Embodiment 41. The kit according to embodiment 40, wherein said expression construct comprises a promoter that provides for expression of said polynucleotide in neurons or glial cells.

Embodiment 42. The kit according to embodiment 39, wherein said one or more containers further comprise a biologically active agent useful in treating neurodegenerative disease or condition.

Embodiment 43. The kit according to embodiment 39, wherein said one or more containers further comprises a biologically active agent useful for disaggregating neurofibrillary aggregates.

Embodiment 44. The method, composition, packaged dosage formulation, or kit according to any one of embodiments 1 to 43, wherein the CyP40 is human CyP40.

Embodiment 45. The method, composition, packaged dosage formulation, or kit according to any one of embodiments 1 to 43, wherein the CyP40 comprises the amino acid sequence of SEQ ID NO:1

Materials and Methods

Protein Purification. Recombinant human P301L tau, CyP40, CyP40 H141E, CyPA, FKBP51, and FKBP52 were cloned into Pet28 plasmids, and then transformed into competent *E. coli* BL21 cells and plated on kanamycin-agar plates and incubated at 37° C. overnight (~16 hours). A single colony was used to inoculate a 10 mL starter culture of LB broth supplemented with kanamycin. After 8-12 hours, starter cultures were used to inoculate 1 L of LB-kanamycin broth and cultures were grown to an OD600 of 0.8 (~3 hrs). At this point, cultures were induced with 1 mM (final concentration) IPTG and grown a further 3 hours. Pellets were spun down at 3500×g for 30 minutes and supernatant was discarded by aspiration. Pellets were then resuspended in Nickel chromatography running buffer (20 mM Tris-HCl pH 8.0, 500 mM NaCl, 10 mM Imidazole) and frozen for up to 3 months at −80° C.

Pellets were then thawed on ice and subsequently lysed by sonication and spun at 50,000×g for 1 hour. After filtration of the supernatant with a 0.02 μm filter, a standard gravity nickel column using Ni-NTA resin (Fisher #PI88222) was performed. TEV protease was then added to the elution fraction, placed into a 3,000 MW cutoff dialysis bag and into TEV buffer overnight at 4° C. The solution was then dialyzed back into nickel chromatography running buffer and a $2^{nd}$ nickel purification column was ran. We then performed size exclusion chromatography using a HiLoad 16/600 Superdex 200 pg column and fractions were pooled and concentrated. Proteins were then dialyzed into appropriate buffer (PBS or Sodium Acetate). Proteins were estimated to be >95% pure by coomassie staining.

Amyloid Beta protein fragment 42 was purchased from Sigma Aldrich (107761-42-2), and mature α-synuclein fibrils were a generous gift from Dr. Vladimir Uversky at USF.

Fibril formation. 50 μM recombinant human tau P301L was incubated in the presence of 12.5 μM low molecular weight heparin (4:1 molar ratio) at 37° C. in 100 mM Sodium Acetate pH 7.0 buffer without agitation for 7 days. Thioflavin T fluorescence was recorded throughout fibrillation in order to confirm plateau of fluorescence. Aβ42 fibrils were formed by suspending the lyophilized protein in minimal 60 mM NaOH and then diluting to a final concentration of 50 μM in PBS buffer. The solution was then shaken at 700 rpm at 37° C. for 5 days.

Thioflavin T Fluorescence Assay. 7.5 μM pre-formed fibril was incubated with 7.5 μM CyP40 protein (wt or mut where indicated) in 100 μM Sodium Acetate pH 7.0 buffer (or PBS for α-synuclein and Aβ42) in a 96-well black clear-bottom plate (Fisher #07-200-525). Final volume before ThT addition was 100 μL per sample. At set time points (0, 1, 3 hours), 7.5 μM Thioflavin T (final concentration) was added and fluorescence read at 440 nm excitation and 482 nm emission in a BioTek Synergy H1 plate reader.

Transmission Electron Microscopy. 10 μL of protein samples were adsorbed onto 300 mesh square mesh copper grids (EMS300-Cu) for 30 seconds. Grids were then washed twice with 10 μL of deionized water and excess water wicked with filter paper. Grids were negatively stained with 4% uranyl acetate for 30 seconds and dried overnight. Grids were viewed using a JEOL 1400 Digital Transmission Electron Microscope and images were captured with a Gatan Orius wide-field camera. Fields shown are representative.

Nanoparticle tracking analysis. At the end of experiments, samples were diluted 10,000 fold into 1 mL of deionized filtered water (0.02 μm). Approximately 300 μL sample was loaded onto the Malvern Nanosight LM10 equipped with a 633 nm red laser. Protein particle data was captured with a Marlin CCD camera in duplicate. Between samples, 500 μL of water was passed through the imaging chamber to clear previous sample. Graphs were generated by Nanosight software.

Circular dichroism (CD) spectroscopy. Far-UV CD measurements were taken using a JASCO J-815 spectropolarimeter. Wt CyP40 and mut CyP40 were dialyzed into 10 mM sodium phosphate buffer, pH 7.5. Proteins were loaded into a 1 mm quartz cuvette and readings were taken at 25° C. Each spectrum is an average of 3 scans from 190-260 nm at 50 nm/min. Buffer spectral curves were subtracted for each protein.

Chymotrypsin-coupled assay. PPIase activity was measured by a chymotrypsin-coupled assay using a synthetic peptide succinyl-Ala-Ala-Pro-Phe-p-nitroanilide (Sigma) as previously described [28] with some modifications. Briefly, the reactions were set up in precooled 1 ml reaction buffer (50 mM Tris-HCl, pH 7.5, 150 mM NaCl, 10 mM $CaCl_2$) by adding 5 μl 1 mM peptide, 1 μl chymotrypsin (1 mg/ml, Sigma), and 0.5 μM purified protein. The absorbance was measured every 20 seconds for 10 min at 410 nm in a Genesys 105 UV-Vis spectrophotometer (Thermo) at 4° C.

iHEK-P301L and sarkosyl soluble analysis. Tetracycline inducible HEK293 cell line (iHEK) was generated by the insertion of human P301L tau 4R0N DNA into a pCDNA 4/TO plasmid vector (Invitrogen). The tau/TO plasmid construct was transfected into the T-REx™ HEK cell line (Invitrogen) which stably express the tetracycline repressor protein. After zeocin selection (200 μg/ml), the colonies were picked up and the expression of Tau was detected by Western blot with and without tetracycline (1 μg/ml).

To investigate the effect of CyP40 on the level of aggregated, insoluble tau, tau expression was induced for 9 days and then transfected with PCMV6-CyP40 (wildtype and H141E mutants) plasmids using Lipofectamine 2000 (Invitrogen) following the manufacturer's instructions. 48 h after transfection, the sarkosyl insoluble fraction of Tau was prepared as previously described [21].

Mouse studies and tissue processing. rTg4510 Mice were injected at 6-months old (N=9 for CyP40, N=8 for GFP), and harvested at 8-months. Mice were perfused using 0.9% saline solution after which brains were removed rapidly. Brains were fixed in 4% paraformaldehyde overnight. Sucrose gradients up to 30% were used and then tissue was sectioned with a sliding microtome to 25 μm thickness.

Viral injection. Using stereotaxic equipment, mice were injected bilaterally into the hippocampus at X=±3.6 Y=−3.5 Z=+2.68. Each injection delivered 2 μL of adeno-associated viral particles serotype 9 tagged with either green fluorescent protein (GFP) or CyP40.

Immunohistochemistry and immunofluorescence. Tissue was stained free floating as previously described [29]. Tissue sections were incubated in PBS supplemented with 10% MeOH and 3% $H_2O_2$ to block endogenous peroxidases. Following PBS washes, tissue was permeabilized by 0.2% Triton-X-100 with 1.83% lysine and 4% serum in PBS for 30 minutes. Tissue was then incubated at room temperature overnight in primary antibody. The following primary antibodies were used, anti-CyP40 (1:2000), T22 (1:700), and anti-H150 tau (1:30000). Following three PBS washes, biotinylated goat anti-rabbit (Southern Biotech) secondary (1:10000) was added for 2 hours. Prior to peroxidase development, an ABC kit (Vectastain) was used to increase visibility. Following PBS washes, tissue was incubated with 0.05% diaminobenzidine plus 0.5% nickel and developed with 0.03% $H_2O_2$. Tissue sections were then mounted and allowed to dry overnight before dehydration in alcohol gradients. Slides were cleared by Histoclear then coverslipped with DPX.

Sections stained for stereology were blocked and permeabilized as described above and incubated overnight with biotinylated NeuN (1:3000) at room temperature. Following PBS washes. ABC conjugation, and peroxidase development tissue was mounted on glass slides and dried overnight. These sections were then counter-stained with cresyl violet (nissl) by incubating with 0.05% cresyl violet briefly and then quickly destaining with 0.3% acetic acid in water prior to dehydration.

For Gallyas silver staining, tissue slices were mounted on glass slides and dried overnight. These slides were then incubated in a 0.003% potassium permanganate solution for 10 min. After rinsing with water the sections were incubated from 1-2 min in a 2.0% oxalic acid solution then rinsed thoroughly in water. Slides were then incubated in a 5.0% sodium metaperiodate solution for 5 min and again rinsed in water. Slides were then treated with an alkaline silver iodide solution (I M sodium hydroxide, 0.6 M potassium iodide, 0.053% silver nitrate) for 1 min, then rinsed three times with a 0.5% acetic acid solution. Staining was developed by combining solutions A (5% sodium carbonate), B (0.024 M ammonium nitrate, 0.012 M silver nitrate, 0.003 M tungstosilicic acid), and C (0.024 M ammonium nitrate, 0.012 M silver nitrate, 0.003 M tungstosilicic acid, 0.25% formaldehyde) in a 2:1:1 ratio, adding B and C to solution A and incubating for 10-30 min. The slides were then rinsed three times in 0.5% acetic acid, then water. The slides were then incubated in gold tone for 3-4 min and again rinsed in water, then a 1% sodium thiosulphate solution for 5 min and a final rinse in water before they were dehydrated and coverslipped using DPX.

Tissue imaging and quantification. A slide scanning microscope (Zeiss) was used to image all tissue. Bright field analysis was performed using Zeiss Neuroquant IAE analysis software. This program was used to outline regions of interest from the entire slide. Then, thresholds were set manually until only positive cells, as determined by the analyzer, were selected with as little non-specific areas selected as possible. Using the batch process option, the Area Ratio of positive cells within the regions of interest was automatically calculated for each stained group.

Statistical Analysis. Analyses were performed using GraphPad Prism version 5.02. Group differences were analyzed with a two-tailed student's t-test. If $P<0.05$, significance is indicated by a single asterisk (*). If $p<0.01$ significance is marked by two asterisks (). If $p<0.001$, significance is shown with three asterisks (*). Error bars represent standard error of the mean (SEM).

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—CyP40 Disaggregates Amyloid Fibrils In Vitro

Figure 1A:
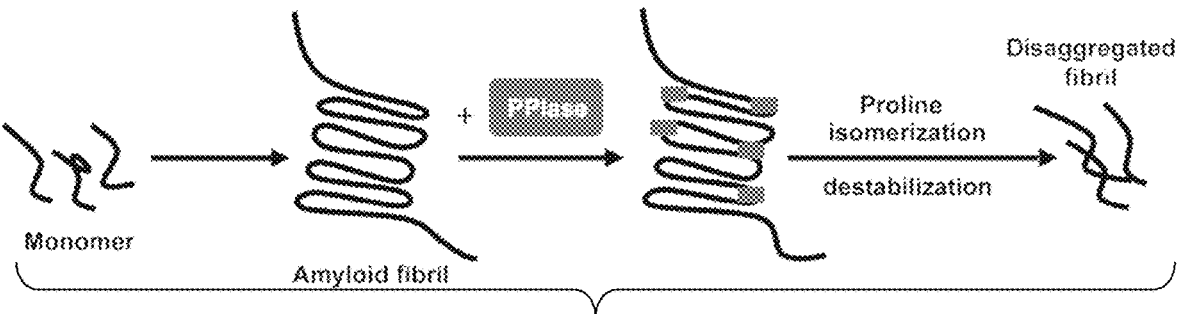
FIGS. 1A-1D. An initial screen of peptidyl-prolyl isomerases identifies CyP40 disaggregase capacity.

For many proteins, amyloidogenesis is significantly affected by structurally flexible proline residues (9,10). Because β-turns are often associated with proline residues (11), the inventors speculated that enzymes capable of twisting these prolines could unravel amyloid structures. The family of cis/trans peptidyl prolyl isomerases (PPIases) is diverse (12), and perhaps most importantly does not require the use of ATP to isomerize proline residues (13). While prolyl isomerization has been implicated in the formation and prevention of protein aggregation (14,15), a role for PPIases in amyloid disaggregation has never been described. Therefore, the inventors hypothesized that discrete PPIases may be able to disaggregate mature amyloid fibrils in a proline-dependent and energy-independent manner (FIG. 1A).

Figure 1B:
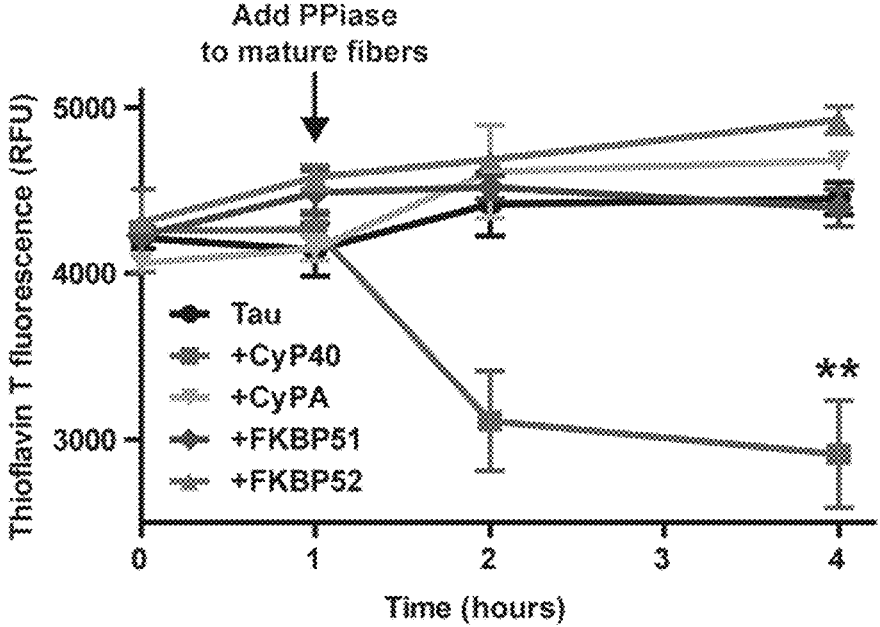
Figure 1C:
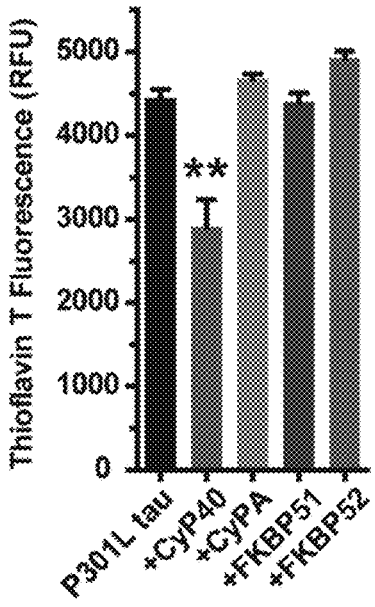
Figure 1D:
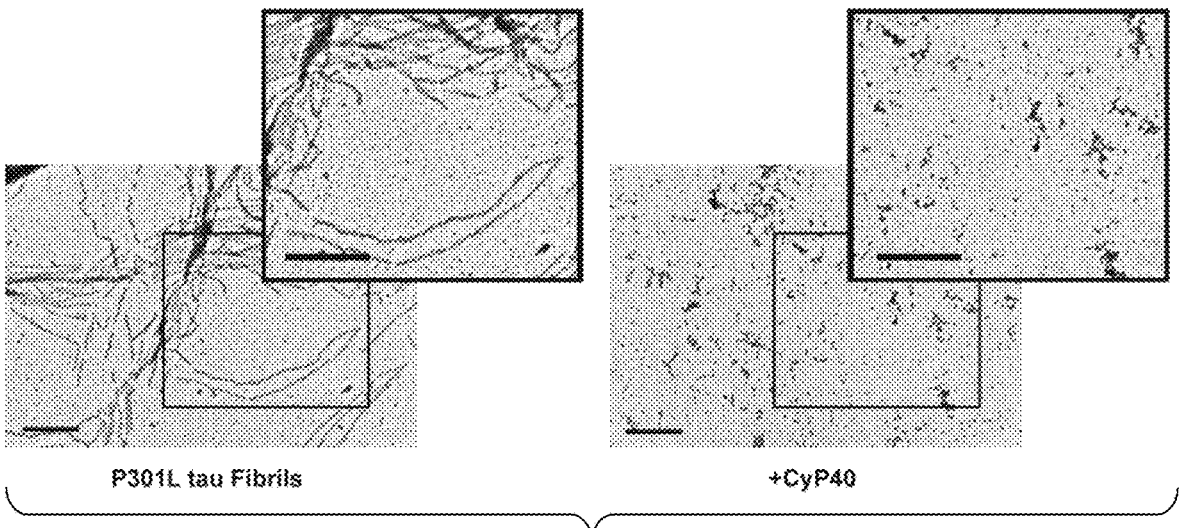

To test this hypothesis, a screen was performed using several well-studied proteins within the PPIase superfamily, including CyPA and the Hsp90 co-chaperones, CyP40, FKBP51, and FKBP52. Individual PPIases were incubated with pre-fibrillized recombinant P301L tau for a period of 3 hours, and Thioflavin T (ThT) fluorescence was measured periodically (FIGS. 1B and 1C). Only CyP40 decreased ThT fluorescence, indicating a reduction in β-sheet secondary structure. Transmission electron microscopy (TEM) of these samples revealed that tau incubated with Cyp40 lacked fibrillar structure compared to control (FIG. 1D). These data indicate that CyP40 is capable of disaggregating amyloid fibrils in vitro.

Example 2—CyP40 Disaggregates Amyloid Fibrils In Vivo

The disaggregase capacity of CyP40 was then evaluated in a mouse model overexpressing P301L tau to determine if the in vitro disaggregase activity of the PPIase had physiological relevance. Hippocampi of rTg4510 mice were injected at 6 months of age with AAV9-GFP or AAV9-CyP40 and harvested at 8 months for histological analysis (FIG. 2A). These ages were chosen so that the disaggregation activity of CyP40 on preformed, mature tau fibrils could be investigated. However, these time points came at the cost of not being able to discern meaningful differences in behavior given the severe hippocampal volume loss observed in these mice by 6-8 months (16-18). CyP40 overexpression significantly decreased relative insoluble tau levels by western blot (FIGS. 2B and 2C), to a level similar to that of a 1-3 month old rTg4510 mouse [19].

CyP40 significantly reduced the levels of total tau (FIGS. 2D and 2E) and even Gallyas silver-positive tau tangles (FIGS. 2F and 2G), hallmarks of tau amyloidosis in human disease. Interestingly, the levels of oligomeric tau, as indicated by T22 immunoreactivity, were also reduced by CyP40 (FIGS. 2H and 2I). This is important because oligomers are known to increase tau neurotoxicity (20-23), perhaps explaining the significantly increased neuronal count of CyP40-injected mice as shown by unbiased stereology (FIGS. 2J and 2K). Collectively, these data indicate that hippocampal CyP40 overexpression reverses tau aggregation, tau oligomer formation and neuronal loss in vivo, even when administered at an age when tau pathology and hippocampal atrophy are quite advanced.

ThT fluorescence and TEM were then used to examine the effects of CyP40 on disaggregation of pre-formed aggregates of other amyloidogenic substrates, including A53T α-synuclein and the β-amyloid 1-42 peptide (Aβ42), pathological hallmarks of Parkinson's disease (PD) and Alzheimer's disease (AD), respectively. While α-synuclein contains proline residues similar to tau, Aβ42 does not, permitting insight into the proline dependence of this mechanism.

Similar to tau, CyP40 decreased ThT fluorescence when incubated with α-synuclein fibrils compared to control (FIG. 3A) and TEM corroborated these results (FIG. 3B). Conversely, CyP40 was unable to disaggregate Aβ42 by either ThT or TEM, hinting at a mechanism involving the PPIase activity and requirement for substrate proline residues (FIGS. 3C and 3D). We then introduced a Nanoparticle Tracking Analysis (NTA) system to analyze the oligomeric profile of each of these proteins. While mature P301L tau fibrils displayed a large abundance of aggregates up to 850 nm, CyP40 co-incubated samples showed a paucity of aggregates greater than 150 nm (FIGS. 3E-1 and 3E-2). Similarly, mature A53T α-synuclein showed abundant aggregates in the 200-400 nm range, while CyP40-treated samples had greatly diminished populations in this size range (FIGS. 3F-1 and 3F-2). NTA confirmed the inability of CyP40 to disaggregate mature Aβ42 fibrils, as large similarly-sized aggregate particles were seen in both control and CyP40-treated samples (FIGS. 3G-1 and 3G-2). These data suggest that CyP40 disaggregase activity is dependent on its prolyl isomerization activity as a means of controlling substrate specificity.

To further explore this mechanism, a mutant of CyP40 lacking PPIase activity was constructed. Mutating histidine 141 to glutamate (H141E) ablated PPIase activity as shown by a chymotrypsin-coupled assay (FIG. 4A). Importantly, the mutation did not significantly alter secondary structure of the protein as evidenced by circular dichroism (FIG. 4B). Wildtype (wt) and mutant (mut) CyP40 were incubated with mature P301L tau amyloid fibrils, and ThT fluorescence was recorded. Although wt CyP40 produced a significant reduction in fluorescence, mut CyP40 was incapable of disaggregating these fibrils (FIG. 4C). Subsequent TEM analysis indicated the presence of intact mature fibrils in both the control and mut CyP40 samples, while wt CyP40 disintegrated the fibrils (FIG. 4D). These findings also rule out the possibility that the effect of CyP40 was the result of a technical artifact brought on by recombinant protein administration facilitating the interaction properties of aggregates with polymers as previously described [24].

To confirm the dependence of CyP40 disaggregation on its prolyl isomerase activity, an inducible cell model overexpressing P301L tau was derived (iHEK). In this model, tau overexpression is induced by tetracycline, and high molecular weight tau, indicative of aggregated, insoluble material, is evident by day 9 and reaches a maximum intensity at 11 days post-induction as demonstrated by SDS-PAGE (FIGS. 4E and 4F). Wt CyP40, mut CyP40, or empty vector were transfected 9 days following tetracycline administration, and sarkosyl insoluble and soluble tau fractions were analyzed. Consistent with the in vitro data, wt CyP40 was capable of reducing insoluble tau levels after 2 days of expression while the isomerase-null mutant and empty vector had little effect (FIGS. 4E and 4F). Collectively, these data indicate that the PPIase activity of CyP40 is necessary for its disaggregation capacity.

Overall, these findings suggest that human CyP40 has a unique capacity to twist key proline residues within the structures of some amyloidogenic proteins [25,26], effectively leading to their disassembly and rendering them less neurotoxic (FIG. 1A). No other PPIase tested had disaggregation activity, possibly due to a unique amino acid expansion in a loop within the isomerase domain of CyP40. If responsible for its disaggregase capacity, this unique expansion could be selectively targeted without disrupting other PPIases, providing a novel mechanism to therapeutically disrupt intractable aggregates. Furthermore, cyclophilins are known to have diverse surface charges, and the unique mixed charge character of CyP40 may facilitate binding with amyloid substrates [27]. Additionally, knowing that an ATP-dependent Hsp70 disaggregase complex exists raises the possibility of an Hsp90/CyP40 disaggregase machine. Because CyP40 contains a TPR domain, it interacts with Hsp90 and this ATP-driven complex may influence disaggregation rate and substrate specificity. These machinery could be critical to the understanding of protein aggregate biology. Moreover, strategies aimed at enhancing disaggregase activity could potentially delay or even reverse pathological advance in several diseases.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. P. Jam-Ampornpan et al., Mechanism of an ATP-independent protein disaggregase: II. distinct molecular interactions drive multiple steps during aggregate disassembly. The Journal of biological chemistry 288, 13431-13445 (2013).
2. L. Goldschmidt, P. K. Teng, R. Rick, D. Eisenberg, Identifying the amylome, proteins capable of forming amyloid-like fibrils. Proceedings of the National Academy of Sciences of the United States of America 107, 3487-3492 (2010).
3. D. Eisenberg, M. Jucker, The amyloid state of proteins in human diseases. Cell 148, 1188-1203 (2012).
4. H. Braak, E. Braak, Neuropathological staging of Alzheimer-related changes. Acta neuropathologica 82, 239-259 (1991).
5. X. Gao et al., Human Hsp70 Disaggregase Reverses Parkinson's-Linked alpha-Synuclein Amyloid Fibrils. Molecular cell 59, 781-793 (2015).
6. M. E. Jackrel et al., Potentiated Hsp104 variants antagonize diverse proteotoxic misfolding events. Cell 156, 170-182 (2014).

7. M. E. Jackrel, J. Shorter, Potentiated Hsp104 variants suppress toxicity of diverse neurodegenerative disease-linked proteins. Disease models & mechanisms 7, 1175-1184 (2014).

8. N. B. Nillegoda et al., Crucial HSP70 co-chaperone complex unlocks metazoan protein disaggregation. Nature 524, 247-251 (2015).

9. T. Chiba et al., Amyloid fibril formation in the context of full-length protein: effects of proline mutations on the amyloid fibril formation of beta2-microglobulin. The Journal of biological chemistry 278, 47016-47024 (2003).

10. A. Abedini, D. P. Raleigh, Destabilization of human IAPP amyloid fibrils by proline mutations outside of the putative amyloidogenic domain: is there a critical amyloidogenic domain in human IAPP? Journal of molecular biology 355, 274-281 (2006).

11. V. Y. Torbeev, D. Hilvert, Both the cis-trans equilibrium and isomerization dynamics of a single proline amide modulate P2-microglobulin amyloid assembly. Proceedings of the National Academy of Sciences of the United States of America 110, 20051-20056 (2013).

12. L. J. Blair, J. D. Baker, J. J. Sabbagh, C. A. Dickey, The emerging role of peptidyl-prolyl isomerase chaperones in tau. Journal of neurochemistry 133, 1-13 (2015).

13. H. Hodak et al., The peptidyl-prolyl isomerase and chaperone Par27 of Bordetella pertussis as the prototype for a new group of parvulins. Journal of molecular biology 376, 414-426 (2008).

14. J. Giustiniani et al., Immunophilin FKBP52 induces Tau-P301L filamentous assembly in vitro and modulates its activity in a model of tauopathy. Proceedings of the National Academy of Sciences of the United States of America 111, 4584-4589(2014).

15. L. J. Blair et al., Accelerated neurodegeneration through chaperone-mediated oligomerization of tau. The Journal of clinical investigation 123, 4158-4169 (2013).

16. J. F. Abisambra et al., Phosphorylation dynamics regulate Hsp27-mediated rescue of neuronal plasticity deficits in tau transgenic mice. The Journal of neuroscience the official journal of the Society for Neuroscience 30, 15374-15382 (2010).

17. K. Santacruz et al., Tau suppression in a neurodegenerative mouse model improves memory function. Science (New York, N.Y.) 309, 476-481 (2005).

18. T. L. Spires et al., Region-specific dissociation of neuronal loss and neurofibrillary pathology in a mouse model of tauopathy. The American journal of pathology 168, 1598-1607 (2006).

19. C. Dickey at al., Aging Analysis Reveals Slowed Tau Turnover and Enhanced Stress Response in a Mouse Model of Tauopathy. The American journal of pathology 174, 228-238 (2009).

20. J. C. O'Leary, 3rd at al., Phenothiazine-mediated rescue of cognition in tau transgenic mice requires neuroprotection and reduced soluble tau burden. Molecular neurodegeneration 5, 45 (2010).

21. M. Ramsden at al., Age-dependent neurofibrillary tangle formation, neuron loss, and memory impairment in a mouse model of human tauopathy (P301L). The Journal of neuroscience: the official journal of the Society for Neuroscience 25, 10637-10647 (2005).

22. M. Usenovic at al., Internalized Tau Oligomers Cause Neurodegeneration by Inducing Accumulation of Pathogenic Tau in Human Neurons Derived from Induced Pluripotent Stem Cells. The Journal of neuroscience: the official journal of the Society for Neuroscience 35, 14234-14250 (2015).

23. S. M. Ward, D. S. Himmelstein, J. K. Lancia, L. I. Binder, Tau oligomers and tau toxicity in neurodegenerative disease. Biochemical Society transactions 40, 667-671 (2012).

24. A. N. Murray, F. L. Palhano, J. Bieschke, J. W. Kelly, Surface adsorption considerations when working with amyloid fibrils in multiwell plates and Eppendorf tubes. Protein science: a publication of the Protein Society 22, 1531-1541 (2013).

25. A. Morimoto et al., Analysis of the secondary structure of beta-amyloid (Abeta42) fibrils by systematic proline replacement. The Journal of biological chemistry 279, 52781-52788 (2004).

26. A. Morimoto at al., Aggregation and neurotoxicity of mutant amyloid beta (A beta) peptides with proline replacement: importance of turn formation at positions 22 and 23. Biochemical and biophysical research communications 295, 306-311 (2002).

27. T. L. Davis at al., Structural and biochemical characterization of the human cyclophilin family of peptidyl-prolyl isomerases. PLoS biology 8, e1000439 (2010).

28. U. K. Jinwal at al., The Hsp90 cochaperone, FKBP51, increases Tau stability and polymerizes microtubules. The Journal of neuroscience: the official journal of the Society for Neuroscience 30, 591-599 (2010).

29. M. N. Gordon, W. A. Schreier, X. Ou, L. A. Holcomb, D. G. Morgan, Exaggerated astrocyte reactivity after nigrostriatal deafferentation in the aged rat. The Journal of comparative neurology 388, 106-119 (1997).

30. M. Gomez-Rio, Caballero M M, Górriz Sáez J M, Minguez-Castellanos A. Diagnosis of Neurodegenerative diseases: The clinical approach. Curr Alzheimer Res., 13(5): 469-474 (2016).

31. Juha Koikkalainen at al. Differential diagnosis of neurodegenerative diseases using structural MRI data. Neuroimage Clin. 11:435-439 (2016).

32. A. John Stoessi. Neuroimaging in the early diagnosis of neurodegenerative disease. Translational Neurodegeneration 1(1):5 (2012).

33. Bryan K. Ward et al. A Structure-based Mutational Analysis of Cyclophilin 40 Identifies Key Residues in the Core Tetratricopeptide Repeat Domain That Mediate Binding to Hsp90. The Journal of Biological Chemistry. 277(42):40799-40809(2002).

34. Elizabeth A. Blackburn et al. Cyclophilin40 isomerase activity is regulated by a temperature-dependent allosteric interaction with Hsp90. Biosci Rep. October; 35(5): e00258 (2015).

We claim:

1. A method for treating a neurodegenerative disease or condition characterized by the presence of neurofibrillary aggregates of the microtubule associated protein tau or α-synuclein in a subject in need thereof, the method comprising administering to the subject an effective amount of peptidyl-prolyl isomerase cyclophilin 40 (CyP40).

2. The method according to claim 1, wherein the method further comprises identifying the subject as one in need of treatment.

3. The method according to claim 1, wherein the disease or condition is Alzheimer's disease, gangliogliomas, gangliocytomas, argyrophilic grain dementia, corticobasal degeneration, dementia pugilistica, frontotemporal dementia with parkinsonism linked to chromosome17, Pick's disease, Hallervorden-Spatz disease, myotonic dystrophy, Niemann-Pick disease type C, Parkinsonism-dementia complex of Guam, postencephalitic parkinsonism, prion diseases, progressive subcortical gliosis, or progressive supranuclear palsy.

4. The method according to claim 1, wherein the CyP40 is administered to the subject orally, nasally, rectally, parenterally, subcutaneously, intramuscularly, intraspinal, intracranially, or intravenously.

5. The method according to claim 1, wherein the CyP40 is administered to the subject as a polynucleotide encoding the CyP40.

6. The method according to claim 5, wherein the polynucleotide is provided in an expression construct.

7. The method according to claim 6, wherein the expression construct is an adeno-associated viral construct.

8. The method according to claim 1, wherein the method further comprises administering to the subject a biologically active agent used in treating neurodegenerative diseases and/or conditions.

9. The method according to claim 1, wherein the subject has the neurodegenerative disease or condition at the time the CyP40 is administered to the subject, and the CyP40 is administered as therapy.

10. The method according to claim 1, wherein the subject does not have the neurodegenerative disease or condition at the time the CyP40 is administered to the subject, and the CyP40 is administered as prophylaxis.

11. A method for disaggregating neurofibrillary aggregates of the microtubule associated protein tau or α-synuclein, the method comprising contacting the aggregates with an effective amount of peptidyl-prolyl isomerase cyclophilin 40 (CyP40) in vitro or in vivo.

12. The method according to claim 11, wherein the contacting is performed in vivo and comprises administering the CyP40 to a human or animal subject, and wherein the CyP40 is administered to the subject orally, nasally, rectally, parenterally, subcutaneously, intramuscularly, intraspinal, intracranially, or intravenously.

13. The method according to claim 11, wherein said contacting is performed in vivo and comprises administering the CyP40 to a human or animal subject, and wherein the CyP40 is administered as a polynucleotide encoding the CyP40.

*   *   *   *   *

SEQUENCE LISTING

<160> NUMBER OF SEQ ID NOS: 1

<210> SEQ ID NO 1
<211> LENGTH: 370
<212> TYPE: PRT

<213> ORGANISM: Homo sapiens

<400> SEQUENCE: 1

```
Met Ser His Pro Ser Pro Gln Ala Lys Pro Ser Asn Pro Ser Asn Pro
1               5                   10                  15

Arg Val Phe Phe Asp Val Asp Ile Gly Gly Glu Arg Val Gly Arg Ile
            20                  25                  30

Val Leu Glu Leu Phe Ala Asp Ile Val Pro Lys Thr Ala Glu Asn Phe
        35                  40                  45

Arg Ala Leu Cys Thr Gly Glu Lys Gly Ile Gly His Thr Thr Gly Lys
    50                  55                  60

Pro Leu His Phe Lys Gly Cys Pro Phe His Arg Ile Ile Lys Lys Phe
65                  70                  75                  80

Met Ile Gln Gly Gly Asp Phe Ser Asn Gln Asn Gly Thr Gly Gly Glu
                85                  90                  95

Ser Ile Tyr Gly Glu Lys Phe Glu Asp Glu Asn Phe His Tyr Lys His
            100                 105                 110

Asp Arg Glu Gly Leu Leu Ser Met Ala Asn Ala Gly Arg Asn Thr Asn
            115                 120                 125

Gly Ser Gln Phe Phe Ile Thr Thr Val Pro Thr Pro His Leu Asp Gly
        130                 135                 140

Lys His Val Val Phe Gly Gln Val Ile Lys Gly Ile Gly Val Ala Arg
145                 150                 155                 160

Ile Leu Glu Asn Val Glu Val Lys Gly Glu Lys Pro Ala Lys Leu Cys
                165                 170                 175

Val Ile Ala Glu Cys Gly Glu Leu Lys Glu Gly Asp Asp Gly Gly Ile
                180                 185                 190

Phe Pro Lys Asp Gly Ser Gly Asp Ser His Pro Asp Phe Pro Glu Asp
            195                 200                 205

Ala Asp Ile Asp Leu Lys Asp Val Asp Lys Ile Leu Leu Ile Thr Glu
        210                 215                 220

Asp Leu Lys Asn Ile Gly Asn Thr Phe Phe Lys Ser Gln Asn Trp Glu
225                 230                 235                 240

Met Ala Ile Lys Lys Tyr Ala Glu Val Leu Arg Tyr Val Asp Ser Ser
                245                 250                 255

Lys Ala Val Ile Glu Thr Ala Asp Arg Ala Lys Leu Gln Pro Ile Ala
                260                 265                 270

Leu Ser Cys Val Leu Asn Ile Gly Ala Cys Lys Leu Lys Met Ser Asn
            275                 280                 285

Trp Gln Gly Ala Ile Asp Ser Cys Leu Glu Ala Leu Glu Leu Asp Pro
        290                 295                 300

Ser Asn Thr Lys Ala Leu Tyr Arg Arg Ala Gln Gly Trp Gln Gly Leu
305                 310                 315                 320

Lys Glu Tyr Asp Gln Ala Leu Ala Asp Leu Lys Lys Ala Gln Gly Ile
            325                 330                 335

Ala Pro Glu Asp Lys Ala Ile Gln Ala Glu Leu Leu Lys Val Lys Gln
            340                 345                 350

Lys Ile Lys Ala Gln Lys Asp Lys Glu Lys Ala Val Tyr Ala Lys Met
        355                 360                 365

Phe Ala
370
```